(12) United States Patent
Sanger

(10) Patent No.: US 8,311,623 B2
(45) Date of Patent: Nov. 13, 2012

(54) SYSTEMS AND METHODS FOR ESTIMATING SURFACE ELECTROMYOGRAPHY

(75) Inventor: Terence D. Sanger, Palo Alto, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 919 days.

(21) Appl. No.: 12/226,373

(22) PCT Filed: Apr. 12, 2007

(86) PCT No.: PCT/US2007/009122
§ 371 (c)(1),
(2), (4) Date: Feb. 5, 2009

(87) PCT Pub. No.: WO2007/120819
PCT Pub. Date: Oct. 25, 2007

(65) Prior Publication Data
US 2009/0209878 A1 Aug. 20, 2009

Related U.S. Application Data

(60) Provisional application No. 60/792,135, filed on Apr. 15, 2006.

(51) Int. Cl.
*A61B 5/0488* (2006.01)

(52) U.S. Cl. ............................................ 600/546

(58) Field of Classification Search .................. 600/434, 600/435, 546
See application file for complete search history.

(56) References Cited

U.S. PATENT DOCUMENTS

| | | | | |
|---|---|---|---|---|
| 4,030,141 A * | 6/1977 | Graupe | ............................ | 623/25 |
| 4,209,860 A * | 7/1980 | Graupe | ............................ | 623/25 |
| 5,265,042 A * | 11/1993 | Smith, Jr. | ...................... | 708/310 |
| 5,679,004 A * | 10/1997 | McGowan et al. | ............ | 434/247 |
| 6,076,011 A * | 6/2000 | Hoover | .......................... | 600/546 |
| 6,280,394 B1 * | 8/2001 | Maloney et al. | ............... | 600/546 |
| 6,487,441 B1 * | 11/2002 | Swanson et al. | ............... | 600/510 |
| 6,532,383 B2 * | 3/2003 | Maloney et al. | ............... | 600/546 |
| 6,785,574 B2 * | 8/2004 | Kajitani et al. | ................ | 600/546 |
| 6,847,737 B1 * | 1/2005 | Kouri et al. | .................... | 382/260 |
| 6,859,663 B2 * | 2/2005 | Kajitani et al. | ................ | 600/546 |
| 7,152,470 B2 * | 12/2006 | Impio et al. | ................. | 73/379.01 |
| 7,369,896 B2 * | 5/2008 | Gesotti | ............................ | 607/49 |
| 7,396,337 B2 * | 7/2008 | McBean et al. | .................... | 601/5 |
| 7,398,255 B2 * | 7/2008 | Lauer et al. | ........................ | 706/8 |
| 7,442,212 B2 * | 10/2008 | Richmond et al. | .............. | 623/25 |
| 7,811,333 B2 * | 10/2010 | Jonsson et al. | ................... | 623/24 |
| 7,834,527 B2 * | 11/2010 | Alvarez Icaza Rivera et al. | ............................. | 310/344 |
| 7,896,927 B2 * | 3/2011 | Clausen et al. | ................. | 623/27 |

(Continued)

OTHER PUBLICATIONS

EMG Onset Detection Using the Max Likelihood Method Stylianous et al. 2003 Summer Bioengineering Conference, Jun. 25-29, Sonesta Beach Resort in Key Discayne, Florida.*

(Continued)

*Primary Examiner* — Max Hindenburg
*Assistant Examiner* — Michael C Stout
(74) *Attorney, Agent, or Firm* — Evans & Molinelli PLLC; Eugene J. Molinelli

(57) ABSTRACT

A rehabilitation device is presented that is inexpensive to produce and is easy to use. The device uses a predictable method to estimate the activity of muscle and therefore provide many ways to train and rehabilitate a person having a prosthetic limb or other neuromuscular disorder.

30 Claims, 5 Drawing Sheets

U.S. PATENT DOCUMENTS

| | | | |
|---|---|---|---|
| 8,108,036 B2* | 1/2012 | Tran | 600/509 |
| 2001/0025146 A1* | 9/2001 | Maloney et al. | 600/546 |
| 2003/0125636 A1* | 7/2003 | Jeong et al. | 600/546 |
| 2004/0088025 A1* | 5/2004 | Gesotti | 607/49 |
| 2004/0106881 A1* | 6/2004 | McBean et al. | 601/5 |
| 2005/0049517 A1* | 3/2005 | Mathew et al. | 600/546 |
| 2005/0082488 A1* | 4/2005 | Mollov et al. | 250/369 |
| 2005/0178201 A1* | 8/2005 | Impio et al. | 73/379.01 |
| 2006/0173364 A1* | 8/2006 | Clancy et al. | 600/485 |
| 2006/0253166 A1* | 11/2006 | Flaherty et al. | 607/48 |
| 2007/0032738 A1* | 2/2007 | Flaherty et al. | 600/545 |
| 2007/0282228 A1* | 12/2007 | Einav et al. | 601/33 |
| 2009/0149779 A1* | 6/2009 | Russo et al. | 600/595 |
| 2009/0221928 A1* | 9/2009 | Einav et al. | 600/544 |
| 2012/0092157 A1* | 4/2012 | Tran | 340/539.12 |

OTHER PUBLICATIONS

Cross-spectral analysis of physiological tremor and muscle activity I Theory and application to unsynchronized electromyogram, Biol, Byberm, 78, 349-357, 1998.*

High-Precision EMG Signal Decomposition Using Communication Techniques, Gut et al. IEEE Transactions on Signal Processing vol. 48, No. 9, Sep. 2000.*

* cited by examiner

SYSTEMS AND METHODS FOR ESTIMATING SURFACE ELECTROMYOGRAPHY

RELATION TO OTHER APPLICATIONS

The present application claims priority to and benefit of U.S. Provisional Patent Application Ser. No. U.S. 60/792,135 entitled "Systems And Methods For Estimating Surface Electromyography", filed 15 Apr. 2006, which is herein incorporated by reference in its entirety for all purposes.

This invention was made partly using funds from the National Institute of Neurological Disorders and Stroke Grant Number NS-041243. The US Federal Government may have certain rights to this invention.

FIELD OF THE INVENTION

The present invention relates to devices that are used to measure muscle activity. In particular, the present invention relates to a system and methods for determining surface electromyography.

BACKGROUND

Surface electromyography (sEMG) is the technique of recording electrical signals from the skin overlying muscles in order to estimate the activity in the muscle beneath. sEMG has been used in the following areas:

1. Research: to measure the activity in muscles during voluntary movement or in response to interventions that might affect muscles, motor control, or other aspects of voluntary or involuntary muscle contraction. During voluntary movement, the sEMG signal is often interpreted as the "intent" of the subject, which may be different from the resulting movement when external forces or constraints are present.
2. Biofeedback: to isolate the activity of individual muscles and provide information to the subject about the state of those muscles. Biofeedback may be used in order to increase activity and thereby strengthen weak muscles, it may be used in order to decrease activity and thereby relax dystonic muscles or muscle spasms, or it may be used to reinforce particular desired patterns of activity of multiple muscles. Biofeedback can be used both for clinical treatment and for training competitive sports.
3. Control: to use the activity of one or more muscles in order to control electromechanical devices. This has been extensively investigated for patients with limb amputations, or with neurological disorders (including spinal cord injury, amyotrophic lateral sclerosis, or stroke) that prevent normal movement. The goal in such cases is the construction of electrically-controllable prosthetic devices. One of the most extreme applications is when sEMG is combined with functional electrical stimulation (FES) so that sEMG signals from one muscle are used to stimulate the contraction of another muscle in order to reinstate some degree of control over paralyzed limbs.

Despite the tremendous promise of sEMG technology, essentially all applications have been severely hampered by the poor quality of sEMG signals. It is generally believed that sEMG provides a "noisy" signal that is of insufficient quality for accurate control. Therefore the quality of research data is poor, use in biofeedback is limited to simple activation or deactivation of muscles, and use in control is limited to simple on-off switches that often require careful tuning and practice in order to achieve reliable performance. Strategies to improve performance have attempted to place multiple sEMG electrodes in order to reduce noise and provide more consistent signals. However, such methods have had limited success and even more limited applicability due to their complexity and the very modest improvement in signal quality.

Inspection of sEMG signals reveals the difficulty with their interpretation (see FIG. 1): the sEMO signal appears to be extremely noisy, yet the resulting force that is generated is much smoother. It seems that the level of noise in the sEMG signal reflects the resulting force much more than the actual values of the sEMG signal. This suggests that one strategy for reading the sEMG signal is to estimate the magnitude of the noise itself.

Current State of the Art

Current methods for interpreting sEMG attempt to estimate the "envelope" of the signal. This corresponds to an assumed model for the generation of sEMG as:

$$sEMG(t)=x(t)*n(t)$$

where at each time t the value of the sEMG signal is the product of an activity level x(t) and Gaussian white noise n(t). Estimation of x(t) is typically achieved by estimating the power in the sEMG signal, because $$E[sEMG^2(t)]=E[x^2(t)n^2(t)]=\sigma^2 x^2(t)$$

where E[ ] indicates the expected value, $\sigma^2$ is the noise variance, and $x^2(t)$ is the square of the current value of the activity level. In practice, this is usually approximated using the absolute value (the positive square root of both sides of the equation) and the expectation operator is estimated by the use of a low-pass filter. We refer to the combination of rectification (absolute value) and low-pass filtering as the "linear method".

FIG. 2 shows another example of sEMG, the true resulting force, and the linear method estimate for several different low-pass filters. From the figure, we see several of the shortcomings of the linear method:

1. Even for very smooth filters, there is still considerable "ripple" in the estimate that is not present in the true force tracing.
2. There is a delay between the onset of sEMG and the reaction of the filter and that is even longer than the delay between sEMG and generation of muscle force.
3. There is a tradeoff between the ability of the filter to respond rapidly to sudden changes in sEMG and the ability to maintain a smooth response. In particular, filters with better responsiveness to change (upper traces) have much higher variability, while filters with lower variability (lower traces) have more sluggish response to changes in sEMG.

The reason for the poor performance of linear filters lies in the method of estimating $E[x^2(t)n^2(t)]$. Since the sEMG signal behaves like modulated white noise, a short time interval of estimation (corresponding to a low-pass filter with higher cutoff frequency) will form a poor estimate of x(t). Yet a longer time interval of estimation (corresponding to a low-pass filter with lower cutoff frequency) will only form a good estimate of x(t) if x(t) is not changing during that interval. If x(t) is changing, then the filter itself determines the maximum achievable frequency response, and this introduces an artificial limitation on the bandwidth of the estimated signal. For example, the smoothest filter response in FIG. 2 occurs for a filter with −20dB cutoff at 1 Hz, so for this filter the output will never contain frequencies above 1 hz, even if the subject in reality is moving much more rapidly. But no matter how smooth the filter is, since the input behaves like white noise the output will behave like filtered noise and thus will remain randomly varying, even if the variation is slow.

Taking these issues into account, we see that the linear method behaves appropriately only if x(t) is unchanging or very slowly changing. Even then, the stability of the output estimate is poor. The technique proposed herein is to take into account the change in x(t) by providing an explicit model for x(t) as a stochastic process. The sEMG signal is then a version of x(t) that has been corrupted by multiplicative noise.

It is desirable to provide improved approaches, including both devices and methods, for treating and rehabilitating patients suffering from disabilities due to limb loss, muscle loss, muscle fatigue, loss of motor neuron activity, loss of neural tissue, neurological disorders, stroke, and other related conditions.

BRIEF DESCRIPTION OF THE INVENTION

The invention provides systems and methods for measuring electrical signals from the skin overlying muscles and estimating the activity of the muscle in a patient having a need for muscle stimulation or muscle training. The invention also provides systems and methods for providing feedback to the patient.

In one embodiment, the invention provides a proportional control system, the system comprising a first signal detector, a first signal amplifier, a first signal filter, a computer processor, wherein the computer processor comprises a software program, the software program comprising an algorithm, the algorithm adapted for estimating the likelihood that the first signal comprises a muscle activity signal and wherein the first signal detector further comprises at least two electrodes. In one preferred embodiment the signal detector is adapted for measuring a surface electromyography (EMG) signal from a human patient. In another preferred embodiment, the first signal filter is a bandpass filter.

In another preferred embodiment, the system further comprises a variable resistor for changing the intensity of the detected first signal. In yet another preferred embodiment, the system further comprises a variable resistor for changing the shift value of the detected first signal. In another preferred embodiment, the system further comprises a variable resistor for changing the drift value of the detected first signal.

In another embodiment the computer processor further comprises a nonlinear filter.

In another embodiment the algorithm estimates the maximum likelihood of the output of the filter using the equation:

$$MLest = \mathrm{argmax}_x p(n|x)$$

wherein MLest is the output of the nonlinear filter and an estimate of the true value of x, x is the unobserved signal to be estimated, n is the observed noisy EMG signals, p is the probability that n occurs given x, and where ML is maximum likelihood. In an alternative embodiment, the algorithm estimates the maximum a posteriori (MAP) estimate of the unobserved signal: argmax p(x|n). The algorithm further comprises a stochastic differential equation selected from the group consisting of $dx=f(x)dt+a(x)dw+b(x)dN1$, $dy=Hydt+CdN2(rx)$, and $p_n(x, t)=(g*p(x, t-1)+v)/K$, where N1 and N2 are stochastic counting processes; dN1 and dN2 are the Ito differentials of these processes; the rate of the process N2 is given by the current value of x multiplied by a fixed gain r; H and C are linear operators; dw is the differential of Gaussian noise (a wiener process); x is the unobserved signal to be estimated; and y is the observed measurement of the outer surface EMG.

In another embodiment the proportional control system further comprises a signal transducer and an output device, the output device selected from the group consisting of an audio speaker, a visual display unit, a haptic device, a computer, a microprocessor, a computer console, and a radio transmitter, and wherein the signal transducer and the output device are in electrical communication with the computer processor.

In another embodiment, the proportional control system further comprises a feedback system, the feedback system comprising a second signal transmitter, and a second signal generator, and a motor, wherein the feedback system is in electrical communication with the computer processor.

In a yet other embodiment the proportional control system further comprises a motorized device, motorized device selected from the group consisting of a vibrator, a massager, a roller, a prosthetic limb device, a device for stimulating muscle, a motorized bicycle, a motor scooter, a motor vehicle, a motorized aircraft, a motorized boat, and a motorized wheelchair.

In a preferred embodiment the proportional control system comprises an algorithm comprising equations selected from the group consisting of equations 31, 32, 33, 34, and 35, wherein the algorithm estimates a complete conditional probability density at any point in time based on a current and all prior observations of a desired signal.

The invention also provides a data processing system, the data processing system comprising a first detector for detecting a first signal, a first signal amplifier, a first signal filter, a computer processor for processing data, storage means for storing data on a storage medium, a first means for initializing the storage medium, a second means for collecting and processing data received from the first signal filter. In one embodiment, the first means comprises a programmable logic circuit configured to prepare the storage means to store collected data. In another embodiment, the second means comprises a programmable logic circuit configured to retrieve information from the storage medium. In a preferred embodiment, the second programmable logic circuit is configured to estimate the likelihood that the first signal comprises a muscle activity signal. In an alternative preferred embodiment the second programmable logic circuit is configured to use a nonlinear filter to determine the most probable or maximum likelihood value of an unknown muscle control or driving signal. In another preferred embodiment, the first detector is adapted for measuring the first signal and wherein the first signal is a surface electromyography (EMG) signal from a subject. In a yet other preferred embodiment the first signal filter is a nonlinear filter. In another embodiment the first signal filter is a bandpass filter.

The data processing system can further comprise a signal transducer. In another embodiment, the data processing system further comprises output means. In a preferred embodiment, the output means is selected from the group consisting of an audio speaker, a visual display unit, a haptic device, a computer, a microprocessor, a computer console, and a radio transmitter. In another preferred embodiment, the signal transducer and the output means are in electrical communication with the computer processor.

Another embodiment of the invention provides the data processing system further comprising a feedback system, the feedback system comprising a second transmitter, and a second signal generator, and a motor. In one preferred embodiment the feedback system is in electrical communication with the computer processor.

One embodiment of the invention provides the data processing system wherein the first detector comprises at least one electrode. In the alternative, the first detector comprises at least two electrodes.

The invention also provides a data processing system comprising a motorized device. In one preferred embodiment, the motorized device is selected from the group consisting of a vibrator, a prosthetic limb device, a device for stimulating muscle, a motorized bicycle, a motor scooter, a motor vehicle, a motorized aircraft, a motorized boat, and a motorized wheelchair.

One preferred embodiment of the invention provides that the second means is configured to estimate the maximum likelihood output of the first signal filter and the maximum likelihood output is calculated according the equation $MLest=\mathrm{argmax}_x p(n|x)$, wherein MLest is the output of the nonlinear filter and is an estimate of the true value of x, x is the unobserved signal to be estimated, n is the observed noisy EMG signal, p is the probability that n occurs given x, and ML is maximum likelihood.

In the alternative, the second means is configured to estimate a maximum a posteriori (MAP) output of the first signal filter and the maximum a posteriori output is calculated using the equation $MAP(x(t))=\mathrm{argmax}\ p(x,t)$ wherein $MAP(x(t))$ is the maximum a posteriori output, x is the activity level of EMG signal, t is an integer, and p is the probability that x occurs at integer t.

In another alternative, the MLest and the MAP(x(t)) can be estimated concurrently.

The invention also provides a processing system wherein the second means is further configured to comprise a model, wherein the model is calculated according to a stochastic differential equation selected from the group consisting of $dx=f(x)dt+a(x)dw+b(x)dN1$, $dy=Hydt+CdN2(rx)$, and $p_0(x, t)=(g*p(x, t-1)+v)/K$.

In another embodiment the second means' configuration comprises a recursive calculation, wherein the recursive calculation is calculated according to an equation, the equation selected from the group consisting of equations 13, 15, 17, and 18, wherein the a recursive calculation estimates a complete conditional probability density at any point in time based on a current and all prior observations of a desired signal.

The invention also provides a use of a processing system for treating or preventing a disorder of the nervous system, the disorder selected from the group consisting of cerebral palsy, brain damage resulting from head trauma, brain damage resulting from oxygen deprivation, paraplegic loss of all or part of a limb, spinal cord injury, amyotrophic lateral sclerosis, and stroke, the processing system comprising the processing system disclosed herein.

In another embodiment the invention also provides use of a processing system for treating or preventing a disorder of the muscle, the disorder selected from the group consisting of, AIDS, sarcopenia, disuse atrophy, glucocorticoid-induced muscle loss, and prolonged spaceflight, the processing system comprising the processing system disclosed herein.

In yet another embodiment the invention also provides use of a processing system for treating a subject having undesired muscle contraction, wherein the undesired muscle contraction is selected from the group consisting of chronic neck pain, back pain, and muscle spasms, the processing system comprising the processing system disclosed herein.

In still another embodiment the invention also provides use of a processing system for facilitating muscle activation in a subject, the muscle activation selected from the group consisting muscle activation during sport, dance, and playing a musical instrument, the processing system comprising the processing system disclosed herein.

The invention further provides information about the level of muscle activity to an individual having a disorder that includes undesired contraction or activation of a muscle. The information may be in the form of vibration, sound, light, a computer display, or other feedback for the purpose of identifying muscle activity and helping to train the individual to reduce the undesired muscle activity. In a preferred embodiment the disorder is selected from the group consisting of a disorder of the central nervous system, a motor-neuron disorder, a neuromuscular disorder, a muscle disorder, cerebral palsy, brain damage, brain damage resulting from head trauma, brain damage resulting from oxygen deprivation, muscle loss, paraplegic loss of all or part of a limb, and the like.

In another embodiment, the invention provides information about the level of muscle activity to an individual with a disorder that includes decreased contraction or activation of a muscle. The information may be in the form of a sensory medium selected from the group consisting of vibration, sound, light, a computer visual display unit, other feedback media, and the like, for identifying muscle activity and training the individual to increase the desired muscle activity. In a preferred embodiment the disorder is selected from the group consisting of a disorder of the central nervous system, a motor-neuron disorder, a neuromuscular disorder, a muscle disorder, cerebral palsy, brain damage, brain damage resulting from head trauma, brain damage resulting from oxygen deprivation, muscle loss, paraplegic loss of all or part of a limb, and the like.

The invention further provides information to an individual about desired patterns of muscle activity and relaxation for assisting the individual with performance of a task.

The invention also provides a method for facilitating muscle relaxation in individuals without a disorder. In one embodiment, information about undesired muscle contraction is provided in order to facilitate maintenance of muscle relaxation in individuals having a disorder selected from the group consisting of chronic neck pain, back pain, and muscle spasms.

The invention also provides a method for facilitating muscle activation in individuals not having a disorder. In one embodiment, information about desired muscle contraction is provided in order to increase activation of desired muscles for activities selected from the group consisting of sport, dance, playing a musical instrument, and the like.

The invention also provides a method for training an individual having a disorder, the method comprising the steps of (i) providing a proportional control system; (ii) positioning the proportional control system in contact to the skin surface of the individual having a neuromuscular disorder; (iii) initiating a movement in the muscle underlying the skin surface thereby stimulating the muscle; (iv) detecting the surface EMG signal; (v) amplifying the sEMG signal; (vi) filtering the sEMG signal; (vii) estimating x(t) using a non-linear filtering algorithm and a predictive model algorithm, the predictive algorithm predicting the output from the muscle and skin; (viii) converting the estimate of x(t) to a digital signal; (ix) providing the digital signal to a driver; (x) activating a motor in a vibrator; wherein the activation of the motor stimulates the skin of the individual having a neuromuscular disorder; and (x) providing feedback to the individual; wherein the individual learns when the muscle was stimulated, the method resulting in training the individual. In a preferred embodiment the disorder is selected from the group consisting of a disorder of the central nervous system, a motor-neuron disorder, a neuromuscular disorder, a muscle disorder, cerebral palsy, brain damage, brain damage resulting from head trauma, brain damage resulting from oxygen deprivation, muscle loss, paraplegic loss of all or part of a limb, and the like. In another preferred embodiment, the feedback is selected from the group consisting of visual, auditory, and tactile feedback.

The invention also provides a method for rehabilitating an individual having a neuromuscular disorder, the method comprising the steps of (i) providing a proportional control system; (ii) positioning the proportional control system in contact to the skin surface of the individual having a neuromuscular disorder; (iii) initiating a movement in the muscle underlying the skin surface thereby stimulating the muscle; (iv) detecting the surface EMG signal; (v) amplifying the sEMG signal; (vi) filtering the sEMG signal; (vii) estimating x(t) using a non-linear filtering algorithm and a predictive model algorithm, the predictive algorithm predicting the output from the muscle and skin; (viii) converting the estimate of x(t) to a digital signal; (ix) providing the digital signal to a driver; and (x) activating a motor in a vibrator; wherein the activation of the motor stimulates the skin of the individual having a neuromuscular disorder; (xi) providing feedback to the individual; (xii) repeating steps (iii) through (xi); the method resulting in the individual being rehabilitated. In a preferred embodiment the disorder is selected from the group consisting of a disorder of the central nervous system, a motor-neuron disorder, a neuromuscular disorder, a muscle disorder, cerebral palsy, brain damage, brain damage resulting from head trauma, brain damage resulting from oxygen deprivation, muscle loss, paraplegic loss of all or part of a limb, and the like. In another preferred embodiment, the feedback is selected from the group consisting of visual, auditory, and tactile feedback. dr

BRIEF DESCRIPTION OF THE FIGURES

FIGS. 2A, 2B, 2C, 2D, and 2E show linear estimates using low-pass filters with −20 dB cutoff at 9, 7, 5, 3, and 1 Hz, respectively.

DETAILED DESCRIPTION OF THE INVENTION

Figure 1:
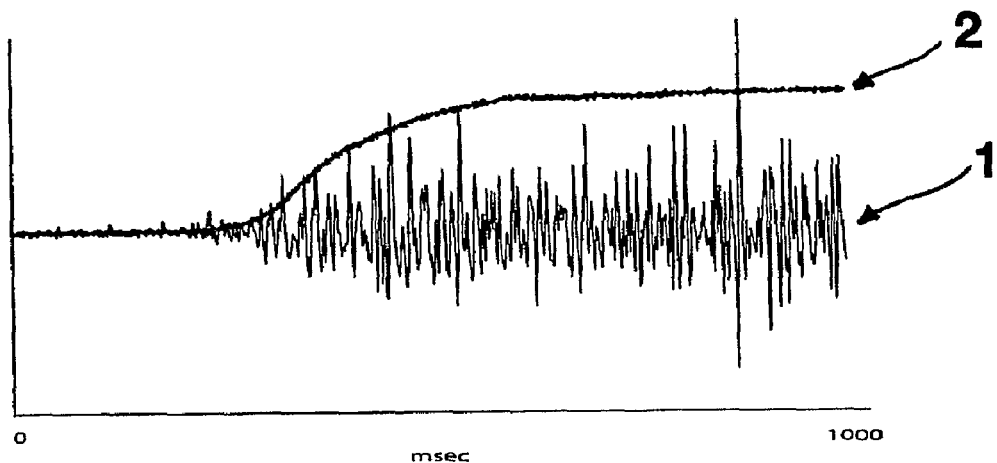
FIG. 1 shows an example of surface EMG (sEMG) signal from biceps ( ) and the torque generated at the elbow (2) during a voluntary contraction.
Figure 2:
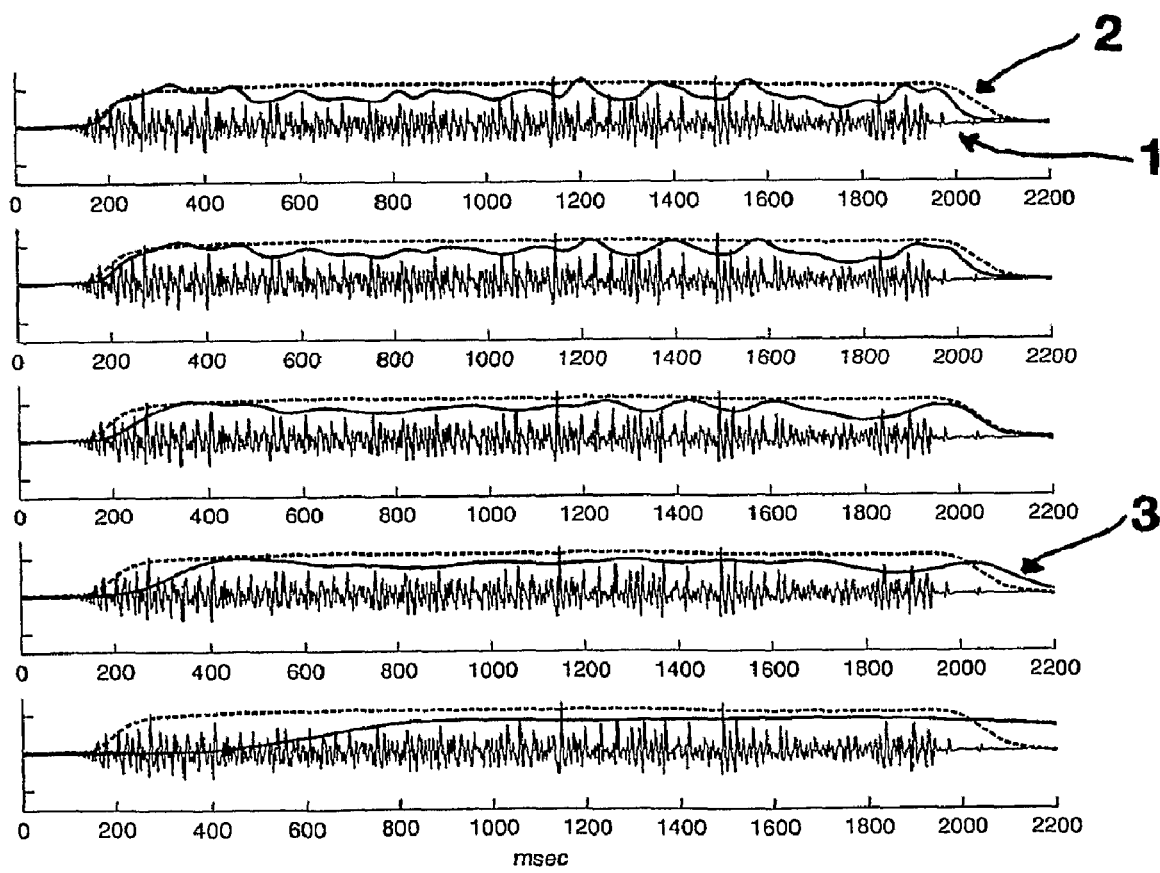
FIG. 2 shows a series of sEMG signals from biceps (1), resulting torque (2), and estimate of muscle activity using linear method (3) over two seconds.

The embodiments disclosed in this document are illustrative and exemplary and are not meant to limit the invention. Other embodiments can be utilized and structural changes can be made without departing from the scope of the claims of the present invention.

As used herein and in the appended claims, the singular forms "a," "an," and "the" include plural reference unless the context clearly dictates otherwise. Thus, for example, a reference to "a signal" includes a plurality of such signals, and a reference to "an algorithm" is a reference to one or more algorithms and equivalents thereof, and so forth.

The invention provides an improved method and system for estimating the surface electromyography (sEMG) compared with the current art. In particular, use of a non-linear filtering algorithm provides a superior estimation result compared with that provided by a linear filtering algorithm. In addition, combining the non-linear filtering algorithm with a predictive model of the output from the muscle and skin providers a superior estimation result compared with that provided by a linear filtering algorithm. In addition, combining the non-linear filtering algorithm with a model of the desired output from the muscle provides a superior signal for the purpose of control of electromechanical actuators or other devices controlled by muscle activity. In addition, an efficient implementation of the nonlinear filtering algorithm provides a method of implementation that is achievable with current computing technology.

Utility of the Invention

The invention can be used in diagnosis, treatment and maintenance of many clinical conditions that result in a disorder of the nervous system, a motor-neuron disorder, or a muscle disorder. In particular, individuals having, for example, but not limited to, cerebral palsy, brain damage, brain damage resulting from head trauma (for example, injuries received during wartime or in civil unrest), brain damage resulting from oxygen deprivation (for example, constriction of the umbilical cord prior to, during, and following birth), muscle loss (for example, AIDS, sarcopenia of old age, disuse atrophy, glucocorticoid-induced muscle loss, and prolonged spaceflight), paraplegic loss of all or part of a limb, muscle fatigue, loss of neural tissue, neurological disorders, stroke, or the like, may use the invention as disclosed herein. The invention may be used in the clinic, such as for use in physiotherapy and/or rehabilitation, or can be used by an individual in a normal home or work environment.

The invention further provides a new recursive algorithm for on-line Bayesian filtering of the sEMG signal. The purpose of this algorithm is to allow the filtered signal to remain constant with low variability during periods of constant drive, but also to permit very rapid "step" changes. The EMG signal is modeled as a filtered random process with random rate, and the likelihood function for the rate evolves in time according to a Fokker-Planck (forward Kolmogorov) partial differential equation is disclosed. A causal on-line algorithm for propagation of the Fokker-Planck equation is provided and its performance on recordings of biceps and triceps activity from single electrodes during isometric contraction is exemplified in the Examples section as well as in Sanger (2007) incorporated herein by reference in its entirety (Sanger (2007) *J. Neurophysiol.* 97: 1839-1845).

Model of the EMG Signal

The surface EMG signal results from propagation of action potentials along muscle fibers that may be close to the skin or buried deep within the muscle. The signal will depend upon the relative timing of potentials, the particular size and shape of the muscle and muscle fiber, the placement of the recording electrode relative to fibers, and the impedance at the skin-electrode interface relative to the amplifier input impedance. It is not attempted here to derive a detailed model for the surface EMG signal, but instead it is proposed that the purpose of filtering is to extract a signal that describes the measured surface EMG signal. This signal is referred to as the "driving signal", although it may not be directly related to the actual neural drive to the muscle.

The instantaneous relation between the latent driving signal x and the resulting EMG signal can be described by a conditional probability density P(EMG|x). Since the driving signal cannot be measured directly, three alternative models for the conditional density are suggested. In particular, exemplary models are provided for the conditional probability of the rectified EMG signal which can be written as emg=|EMG|, since the rectified EMG signal is commonly used in current estimation algorithms.

Under the assumption that the rectified EMG signal results from random depolarization events of multiple muscle fibers, then the average amplitude in a small time window will be proportional to the number of depolarization events during that time. The number of events n can be modeled as a Poisson process so that one can write $$P(emg|x) \approx x^n e^{-x}/n! \qquad (1)$$

where x is the average rate of events for the whole muscle and thus represents the unknown driving signal, and n is an integer that is proportional to the magnitude of the rectified EMG signal. This model ignores the considerable complexity due to filtering properties of the soft tissues, electrode placement, action potential shape, and many other physical effects. This model is referred to as the "Poisson measurement model." The Poisson model with rate described by a stochastic differential equation (see below) has been shown to be a useful model of communications and other nonstationary processes (Boel and Benes (1980) *IEEE Trans. Info. Theory* 26: 561-575).

Empirical observation of the EMG signal has led to the common assumption that it can be described as amplitude-modulated zero-mean Gaussian noise (Hogan and Mann (1980a) *IEEE Trans. Biomed. Eng.* 27: 382-395). In this case:

$$P(EMG|x) = \exp(-EMG^2/2x^2)/(2\pi x^2)^{1/2} \qquad (2)$$

For the rectified EMG signal this function is only defined for values of emg>0, so:

$$P(emg|x) = 2 \cdot \exp(-emg^2/2x^2)/(2\pi x^2)^{1/2} \qquad (3)$$

This model is referred to as the "Half-Gaussian measurement model."

Close observation of the EMG signal has suggested that the density may be better approximated by a Laplacian density (Clancy and Hogan (1999) *IEEE Trans. Biomed. Eng.* 46: 730-739):

$$P(EMG|x) = \exp(-|EMG|x)/2x \qquad (4)$$

which for the rectified EMG signal is given by:

$$P(emg|x) = \exp(-emg/x)/x \qquad (5)$$

Since this is an exponential distribution (with rate 1/x) this model is referred to as the "Exponential measurement model".

It should be noted that all three models are intended to describe the empirically-measured signal; they do not provide a detailed model for the physiological processes responsible for generating the EMG signal. For all three models, the expected value of the rectified EMG signal given x is E[emg|x]=x, and the average value of the rectified EMG signal is thus an unbiased estimator of the driving signal x. If the driving signal is constant, then the law of large numbers states that the average of the rectified EMG signal will approach the true value of x if it is averaged over sufficiently long periods of time.

However, when the driving signal x is time-varying one cannot use the law of large numbers since estimates must be rapid enough to keep up with changes in x. This is the justification for using a low-pass linear filter to estimate x from the rectified EMG signal. However, low-pass filters have an undesirable property: rapid response to change requires a high bandwidth, but high bandwidth will not remove rapid variations in the EMG signal that are unrelated to the driving signal x. Therefore an improved estimator for x will have both rapid response and adequate rejection of irrelevant components of the EMG signal.

Model of the Driving Signal

The driving signal is disclosed herein in terms of a stochastic model. Since the resulting estimate will fit this model, the model should be selected based upon the intended purpose of the estimate. For instance, if the purpose is to estimate joint torque then a model that fits the temporal statistics of torque should be used. If the purpose is to control a mechanical device, then a model that matches the allowable variation in the control signal should be used. A flexible model is chosen that is intended to capture two properties useful for both control and biofeedback: (1) changes in the driving signal are almost always smooth, and (2) large jumps may occur at unpredictable but infrequent intervals. Although the model is implemented in discrete time, it is convenient to write it as a continuous-time stochastic differential equation:

$$dx = \alpha dW + (U-x) dN_\beta \qquad (6)$$

where the equation is to be interpreted in the Ito sense, dW is the differential of standard Brownian motion, $dN_\beta$ is the differential of a counting process with rate β events per unit time, and U is a random variable uniformly distributed on [0,1]. Most of the time, $dN_\beta=0$ so that this reduces to $dx=\alpha \times dW$ which is a random walk. At intervals determined by the rate constant β, the value of x(t) will be replaced by U(t) which corresponds to a jump to a new randomly-selected value of x.

In order to maintain x(t) within the interval [0,1], we further assume:

$$dx = \begin{cases} (1-x)\delta(t-t_0) & \text{if } x(t_0) > 1 \\ (0-x)\delta(t-t_0) & \text{if } x(t_0) < 0 \end{cases}$$

where δ(t) is the Dirac delta function. This equation forces x(t) to remain within the interval [0,1]. Because of this requirement, the Fokker-Planck (forward Kolmogorov) equation for the evolution of the density of x(t) will not have a closed-form solution. However, an approximate solution is given by:

$$\partial p(x,t)/\partial t = \alpha \partial^2 p(x,t)/\partial x^2 + \beta(1-p(x,t)) \qquad (7)$$

The term $\partial^2 p(x,t)/\partial x^2$ is the density evolution for a diffusion process. β indicates the probability of a jump to an arbitrary value of x. As time progresses, β causes p(x,t) to converge exponentially to 1 as the chance of not having jumped to an arbitrary value of x becomes vanishingly small.

Recursive Density Propagation

The novel recursive algorithm and discrete-time approximation here are related to an algorithm developed for nonlinear state estimation (Challa and Bar-Shalom (2000) *IEEE Trans. Aerospace and Elec. Systems* 36: 309-315). However, the previous algorithm was not applied to bioelectric signals, it was not implemented using the efficient discrete approximation that we show below, and it was not based upon a statistical state estimation model using any of the models given above (exponential, Gaussian, or Poisson).

Given a single measurement of emg(t) (rectified EMG signal) at time t, the function P(emg(t)|x(t)) specifies the likelihood of each possible value of x(t) given that particular measurement. Since x(t) is a random variable, Bayes' rule gives the posterior density:

$$P(x(t)|emg(t))=P(emg(t)|x(t))*P(x(t))/P(emg(t)) \quad (8)$$

Where P(x(t)) is the probability density for x(t) immediately prior to the measurement of emg(t). The maximum a posteriori (MAP) estimate of x is found by maximizing P(x|emg), and it is common practice to ignore the denominator term since it is independent of x(t). It is sometimes helpful to include an additional term:

$$P(x(t)|emg(t)) \approx ((1-\gamma)P(emg(t)|x(t))*P(x(t))+\gamma)/C \quad (9)$$

where the small constant γ indicates the probability that the measurement model or the measurement itself are incorrect, and the constant C is chosen to make the density integrate to 1.

In general, the prior P(x(t)) will depend upon the entire past history of measurements, so one can make this dependence explicit by writing P(x(t)|emg(s); s<t). Estimation of P(x(t)) can be performed using a recursive algorithm based on discrete-time measurements, where t is an integer. In discrete time, the goal is to calculate P(x(t)|emg(t), emg(t−1), ...) and using Bayes' rule:

$$P(x(t)|emg(t),emg(t-1), \ldots) = P(emg(t)|x(t))P(x(t)|emg(t-1),emg(t-2), \ldots)/C \quad (10)$$

where C is a constant chosen so that the density integrates to 1, P(emg(t)|x(t)) is given by one of the measurement models in section (a) above, and the standard assumption has been made that successive measurements of the EMG signal are conditionally independent given x(t).

From the previous step of the recursion, one obtains an estimate of P(x(t−1)|emg(t−1), emg(t−2), ...) which can be written as p(x,t−1). It is now necessary to estimate the conditional density of x at time t, but immediately before the measurement of emg(t). To simplify notation, write this density as p(x,t−) which is calculated by propagating the density of p(x,t−1) forward in time by one sampling interval This can be accomplished by numerical integration of the Fokker-Planck equation. In discrete time, this equation is approximated by $$p(x,t-) \approx \alpha \partial^2 p(x,t-1)/\partial x^2 + \beta + (1-\beta)p(x,t-1) \quad (11)$$

(The original values of α and β must be multiplied by the sampling interval Δt, and the density p(x,t) must be renormalized to have integral 1 after each step.) When x is discretized into bins of width ε (so that p(x,t−) is represented as a histogram with N=max(x)/ε elements), the first term can be approximated using second-differences (suppressing the time index for clarity):

$$\partial^2 p(x)/\partial x^2 \approx \alpha p(x-\epsilon) + (1-2\alpha)p(x) + \alpha p(x+\epsilon) \quad (12)$$

so that now:

$$p(x,t-) \approx \alpha p(x-\epsilon, t-1) + (1-2\alpha)p(x,t-1) + \alpha p(x+\epsilon, t-1) + \beta + (1-\beta)p(x,t-1) \quad (13)$$

where α is the diffusion "drift" rate and β is the Poisson "jump" rate for the driving signal model. As soon as a new measurement emg(t) is available, one can calculate:

$$\begin{aligned} p(x, t) &= p(emg(t)|x(t))p(x, t-)/C \\ &= P(emg(t)|x(t))(\alpha p(x-\epsilon, t-1) + (1-2\alpha) \\ &\quad p(x, t-1) + \alpha p(x+\epsilon, t-1) + \beta + (1-\beta) \\ &\quad p(x, t-1))/C \end{aligned} \quad (14)$$

At the first step, p(x,0) can be initialized to a constant (uniform density). At each step, the denominator constant C is chosen to maintain normalization of the density so ∫p(x,t) dx=1.

The MAP (Bayes) estimate of x(t) at each step is:

$$MAP(x(t)) = \arg\max p(x, t) \quad (15)$$

$$= \arg\max P(x(t)|emg(t), emg(t-1), \ldots) \quad (16)$$

Recursive Algorithm

The full algorithm can be summarized as follows:
1. Initialize p(x,0)=1;
2. Forward propagate p(x,t−)≈αp(x−ε,t−1)+(1−2α)p(x,t−1)+αp(x+ε,t−1)+β+(1−β)p(x,t−1); (13)
3. Measure the rectified EMG signal;
4. Calculate the posterior likelihood function P(x,t)≈P(emg|x)p(x,t−); (17)
5. Output the signal estimate MAP(x(t))=argmax P(x,t); (15)
6. Divide p(x,t) by a constant C so that ∫p(x,t)dx=1;
7. Repeat from step 2;

The measurement model P(emg|x) can be chosen to be one of the three models proposed in section (a). For example, for the exponential model step 4 is given by:

$$P(x,t) = (((1-\gamma)/x)e^{(-emg/x)} + \gamma)p(x,t-) \quad (18)$$

There are four free parameters: α, β, γ, and ε. α specifies the expected rate of gradual drift in the signal, in signal units per unit time. β specifies the expected rate of sudden shifts in the signal, in number of expected shifts per unit time. γ specifies the measurement uncertainty, as probability of error per single measurement. ε=m/N specifies the bin width for discretization of the estimate x, where m is the maximum value of x. In the results shown below, α=0.001 Δt, β=10$^{-24}$ Δt, γ=0, ε=m/50, and the sample rate is 1000 Hz (Δt=0.001 seconds). These values were selected empirically by testing on a different data set. The very low value of β represents the assumption that large shifts in the estimate independent of all prior measurements are extremely unlikely. However, β should not be zero because it allows shifts to occur even when prior measurements make these unlikely. (For efficient implementation it is helpful to clip the rectified input signal so that rare high values do not lead to an inappropriately large value of m. Otherwise, the algorithm will attempt to estimate the conditional density for these rare values, but it is unlikely that there will be enough data to do so accurately. In the examples, clipping has been chosen to eliminate samples greater than 3 standard deviations from zero.)

Additional models used in the invention are disclosed below.

Model of sEMG Activity

An important element of the innovation is the construction of a generative model of sEMG activity. This model can be derived in several ways. When used for purposes of control, the model should be constructed so that it has the desired properties of the control signal we seek to extract. We propose that this process can be used to find signals that have much more interesting and useful structure than the current typical assumption of bandlimited spectrum. For example, we can define a desired signal as being constant most of the time with occasional large jumps, using the following stochastic differential equation:

$$dx=f(x)dt+b(x)dN \quad (19)$$

where N is the Ito differential of a Poisson counting process. Similarly, we can define a desired signal that can make small smooth changes using the following equation:

$$dx=f(x)dt+a(x)dw \quad (20)$$

where dw is the Ito differential of a Gaussian random walk. We propose that for sEMG, as well as for many other types of biological and nonbiological signals, it makes sense to incorporate both types of change, so that $$dx=f(x)dt+a(x)dw+b(x)dN \quad (21)$$

This equation indicates that x(t) is influenced by three factors (i) a deterministic drift term f(x), (ii) a smooth random drift term a(x)dw, and (iii) a non-smooth jump process b(x)dN. The advantage of this model is that it avoids the tradeoff between smoothness and responsiveness. The behavior of the control signal can be as smooth as needed while still permitting sudden and rapid jumps when necessary.

It is possible to derive the same general form for the generative model based on the presumed mechanism of generation of sEMG signals. It is assumed that the signal at the skin surface is a low-pass filtered version of a train of muscle fiber action potentials, where the action potentials are spatially and temporally distributed. It is assumed that the probability of firing at any point along a single fiber can be described as a Poisson process with variable rate proportional to x(t), and that we seek to estimate the rate x(t). It is further assumed that $0<=x(t)<=1$, representing the idea that muscle activity cannot be negative and that activity has an upper bound. Assume that there are N fibers that contribute to the sEMG signal present at a single electrode, and let $s_i(t)$ be a random variable that is the integer number of spikes that occur on fiber i (i=1 ... N) during time interval $(t, t+\Delta t)$. Let h(i,t) be a multi-input single-output linear filter. The model of surface EMG as a function of fiber activity is then:

$$sEMG(t)=\Sigma_i h(i,t)*s_i(t) \quad (22)$$

where "*" indicates convolution. The number of spikes on each fiber is given by a Poisson process with rate proportional to x(t). Each fiber may have a different baseline firing rate $r_i$, so the Poisson rate for fiber i is given by $$\lambda_i(t)=r_i x(t). \quad (23)$$

Note that a linear combination of spike counts from multiple Poisson processes is itself a Poisson process. So the sEMG model is equivalent to:

$$sEMG(t)=h(t)*s(t) \quad (24)$$

where h(t) is a single-dimensional linear filter and s(t) is the spike count from a fictive Poisson process that represents the linear combination of activity of all sensed muscle fibers. The Poisson rate for this model remains proportional to x(t) and is given by $$\lambda(t)=rx(t). \quad (25)$$

If h(t) is a low-pass filter, it will effectively average over many successive time intervals. An average of a large number of Poisson processes will behave like a Gaussian process, and therefore the predicted output of this model is not significantly different from the model on which the linear method is based. However, the Poisson model allows a nonlinear maximum-likelihood estimator of the spike rate to be used, and this estimator will turn out to be superior to the linear estimator that is predicted to be optimal for the Gaussian model. This is particularly true when the low-pass cutoff of h(t) is much higher than the maximum voluntarily generated frequency, as is most likely the case for human movement. For example, sEMG signals may contain power that changes with voluntary activity up to about 3 kHz, while the maximum frequency of voluntary movement is normally less than 20 Hz.

Nonlinear Filter

Since x(t) is itself a random process, we can write the following (Ito) stochastic differential equation:

$$dx=f(x)dt+a(x)dw+b(x)dN1 \quad (26)$$

where f(x) represents the deterministic change in x, a(x) represents the "drift" or diffusion of x, and b(x) represents the magnitude of sudden "shifts" in x. For example, f(x) might represent a tendency for x to decay over time due to fatigue. a(x) might indicate that random drift in x (due to the diffusion process dw) is greater at higher levels of activity. b(x) might indicate that sometimes there is a sudden and immediate change in x (due to the counting process dN1). dw is assumed to be the differential of a stationary Gaussian random walk, while dN1 is assumed to be the differential of a stationary Poisson counting process. In other words, the variance $\sigma^2$ of dw and the rate $\lambda$ of dN1 are assumed to be constant.

The stochastic differential equation (26) is a predictive model of the output from the muscle and skin.

Let the matrix H be such that dy/dt=Hy+Cu is a state-space realization of the linear filter y(t)=h(t)*u(t). Then we can write:

$$dy=Hydt+CdN2(rx) \quad (27)$$

where H and C are linear operators (matrices) and dN2(rx) is the differential of a Poisson counting process with rate given by rx(t).

The stochastic differential equation (27) is a predictive model of the corruption by noise from the muscle, skin, and other tissue.

Finally, we have the observed output of the system in terms of the measured surface EMG activity:

$$sEMG(t)=Dy \quad (28)$$

where D is a linear operator (vector) that specifies the observation of the hidden variable y. The full system is a pair of coupled stochastic differential equations. The generative model is therefore:

dx=f(x)dt+a(x)dw+b(x)dN1
dy=Hydt+CdN2(rx)
sEMG(t)=Dy

For discrete-time estimation, we can write the general form:

$\Delta x=f(x)+a(x)n+b(x)s_1$
$\Delta y=h(y)+c(y)s_{2(rx)}$
sEMG(t)=d(y)

In this case, n is a Gaussian random variable with mean zero and variance $\sigma^2$, and $s_1$ and $s_2(rx)$ are independent Poisson random variables. It is understood that x is bounded by 0 and 1. This model is unique and innovative, and it has not previously been suggested as a model for sEMG activity. It is novel in proposing a model for both the underlying signal to be extracted (x(t)) as well as the relation between sEMG and that signal.

Estimation of x(t) from observed values of sEMG(t) would ordinarily proceed in two steps:
1. Prediction: given the estimated value of x(t−1), estimate x(t) from the ordinary differential equation dx=f(x) dt.
2. Observation: given the observed value of sEMG(t), modify the estimate of x(t).

These steps are equivalent to the linear method, if step 2 uses a linear estimate and N2(t) is assumed to be equal to x(t).

A central innovation of the novel method disclosed herein is that the entire probability density p(x,t) is estimated at each point in time. This is similar to the idea behind the Fokker-Planck equation for propagation of the probability density in stochastic differential equations, but here this type of equation is used for estimation, and the coupled equations proposed are considerably more complex. Therefore the following two-step process is proposed:
1. Prediction: given the estimated value of p(x, t−1), estimate $p_0(x,t)$ using dx=f(x)dt+a(x)dw+b(x)dN1. $p_0(x,t)$ is the estimated a priori density just before the observation.
2. Observation: given the observed value of sEMG(t), calculate the a posteriori density p(x,t)=p(x|sEMG(t), $p_0(x, t)$) using Bayes rule.

Prediction Step

The update equation for the prediction step is given by $$dx = f(x)dt + a(x)dw + b(x)dN1 \quad (26)$$

which represents the combination of a deterministic component f(x), a drift component a(x), and a shift component b(x). For simplicity, assume that f(x)=0 (which ignores fatigue and other time-dependent issues). Assume also that a(x)=1, which corresponds to saying that for any value of x, there is the same chance of drift to nearby values of x. Note that this is only an approximation, since x(t) is bounded by 0 and 1. Assume also that b(x) is such that x may jump instantaneously and with equal probability to any possible value between 0 and 1 whenever jumps in N1 occur. Therefore we can write:

$$p_0(x, t) = (g * p(x, t-1) + v)/K \quad (29)$$

where g is the probability density of the Gaussian process dw, v is the Poisson rate of the process N1, and K is a normalization constant. The first term g*p is a standard diffusion process.

The initial state is assumed to be uniform, so that p(x,0)=constant.

Observation Step

D, C, and H are in general unknown. In some cases, these operators could be estimated from known input-output data. For example, if there are records of sEMG and generated muscle force, the force may be taken as a surrogate (and delayed) estimate of x(t) and this could be used to estimate D, C, and H. However, in other cases such records are not available. Therefore the following rough approximations are made: C=1, and H is a filter with low-pass cutoff higher than the sampling frequency. The filter H can be a bandpass filter or equivalent thereof. Other filters are know to those of skill in the art. In this case, the output of the filter H will be zero whenever dN2 is zero, and the output of filter H will go briefly positive and then negative whenever dN2 jumps. Therefore the absolute value of y (and sEMG) will be (on average) proportional to dN2. Since the estimator occurs in discrete time, the following approximation is:

$$abs(sEMG) = D\Delta N2 \quad (30)$$

where $\Delta N2$ is a Poisson process with time-varying rate given by rx(t). Let n be the largest integer less than abs(sEMG)/D. Then from the equation for a Poisson density we can write:

$$p(n|x) = x^n e^{-x}/n! \quad (31)$$

Using Bayes' formula, we can write:

$$p(x|n) = p(n|x) * p(x)/\text{constant} \quad (32)$$

and this gives the observation update rule:

$$p(x, t) = x^n e^{-x} * p_0(x,t)/\text{constant} \quad (33)$$

where the constant is chosen so that $\int p(x,t)dx=1$. At any point in time we can find the maximum likelihood (ML) estimate of x(t) as:

$$ML\text{est}(x) = \text{argmax}_x p(x|n) \quad (34)$$

and MLest(x) is the output of the nonlinear filter.

We can thus write the full algorithm as an iterative process that alternates between two steps:
1. Prediction Step:
   $p_0(x,t) = (g*p(x, t-1)+v)/K$
   $p_0(x,0) = \text{constant}$
2. Observation Step:
   n=ceil(abs(sEMG)/D)
   $p(x, t) = x^n e^{-x} * p_0(x,t)/\text{constant}$
   $ML\text{est}(x) = \text{argmax}_x p(x,t)$ In discrete systems, $p_0(x,t)$ is a vector of probabilities at each discrete time t for each discrete quantized level $x_j$ of x. Therefore we can write
1. Prediction Step:
   $p_0(t) = Gp(t-1) + v/K$
   $p_0(0) = \text{constant}$
2. Observation Step:
   n=ceil(abs(sEMG)/D)
   $p_j(t) = x_j^n e^{-x_j} p_0(x_j,t)/\text{constant}$
   $ML\text{est}(x) = \text{argmax}_j p_j(t)$ Using diag($x_j$) to indicate the diagonal matrix with elements $x_j$, we can write the complete algorithm as a discrete time-varying Markov process:

$$p_0(t) = G\,\text{diag}(x_j^n)\text{diag}(e^{-x_j})p_0(t-1)+v/K \quad (35)$$

Where we assume that $p_0$ is maintained normalized to have sum of 1. Note that the matrices G and diag($e^{-x_j}$) are constant and can be precomputed. This therefore leads to a very efficient computational algorithm that can be easily implemented in software (see below) or hardware.

The embodiment described above uses a Poisson statistics model for the muscle activity as a function of activation. In another embodiment, a Gaussian statistics model and likelihood function can be used. In another embodiment, other distributions can be used, including the exponential distribution.

The time-varying Markov process can comprise any number of levels. In one example eight levels are followed. In another example, sixteen levels are followed. In another example 32 levels are followed. In another example 64 levels are followed. In another example 128 levels are followed. In yet another example, 256 levels are followed. In another example 512 levels are followed. In another example 1024 levels are followed.

Free Parameters

There are several free parameters that need to be chosen in order to implement the algorithm: r, D, v, and $\sigma^2$. Also note that there is no natural scale for x. In practice, an appropriate scale for x (units of force, torque, or some task-dependent units) is chosen and then r provides a free parameter that allows scaling. Similarly, there are no natural units for abs (sEMG) and D scales this value.

r and D enter into the equation for the Poisson density as $x^n e^{-x}$ since they provide arbitrary scaling units to both x and n. In fact, the Poisson density is always maximized when x=n, so once the units of x and sEMG are fixed, r will be proportional to D. The value of D does affect the behavior of the algorithm. In particular, large values of D will broaden the likelihood function $x^n e^{-x}$ while small values will narrow the function. The broader the function, the less certainty there is about the correct value of x for any single observation of sEMG. Therefore the choice of D controls the level of confidence in single observations.

v represents an assumption about the probability of sudden changes in x. Larger values of v allow More frequent sudden changes, while smaller values permit sudden changes only at longer intervals. This represents a prior assumption about the nature of the underlying control signals, and it can be used to tune the behavior of the filter in order to permit or prevent jumps in output.

$\sigma^2$ represents an assumption about the speed of gradual changes in x. Larger values of $\sigma^2$ allow a greater speed of drift, while smaller values enforce relatively constant output. For example, a small value of $\sigma^2$ with a large value of v will lead to piecewise constant output, while a large value of $\sigma^2$ with a small value of v will lead to smoothly-varying output. The ability to independently choose parameters for the rate of drift and the frequency of shifts distinguishes this algorithm from linear methods. In linear methods, minimizing drift eliminates the possibility of rapid shifts. No such tradeoff exists for the ML estimation method.

The Bayesian estimation algorithm is a new algorithm for recursive estimation of the driving signal of the surface EMG signal. It is very flexible and can be adapted to use different models of the statistical distribution of the EMG signal and different assumptions on the statistics of the driving signal. The primary advantage of the new algorithm is the possibility for very smooth output signals without eliminating the possibility of sudden and large changes in value. Therefore the output signal may be more useful for prosthetic control or biofeedback, and it may better indicate the volitional drive to muscles.

Another important advantage of the algorithm is the flexibility in implementation. As derived above, there are four parameters that can control the drift, jumps, measurement uncertainty, and quantization. Increasing the measurement uncertainty will require a larger number of consistent data samples before a change in output will occur, but will also lead to a higher ultimate likelihood. So this provides a straightforward method for trading off uncertainty against response time, with the assurance that the resulting filter will have the minimum possible response time.

The algorithm belongs to a class of nonlinear filters that has been extensively studied (Smith and Brown (2003) *Neural. Comput.* 15: 965-991; Twum-Danso and Brockett (2001) *Neural Netw.* 14:835-844). In order to reduce computational requirements, forward propagation of the conditional density p(x,t) can be implemented using the "Particle Filter" algorithm (Brockwell et al. (2004) *J. Neurophysiol.* 91: 1899-1907; Brown et al. (2001) *Proc. Natl. Acad. Sci. U.S.A.* 98: 12261-12266), although particle filters remain very time-consuming to implement. Because of the specific assumptions about the form of the stochastic differential equation and simplifying assumptions used in calculating the discrete-time approximation, a much more efficient closed-form approximate solution can be found (Challa and Bar-Shalom (2000) *IEEE Trans. Aerospace and Elec. Systems* 36: 309-315). This significantly reduces computational burden and allows the algorithm to be implemented in portable hardware. For example, with the algorithm running under MATLAB (Mathworks, Natick Mass.) on a 1.2 GHz PowerPC computer (Apple Computer, Inc. Sunnyvale Calif.), filtering a 10-second signal requires approximately 3 seconds. A compiled implementation of the algorithm on the same computer can perform estimates in real-time at 100 Hz (producing one estimate for every 10 input samples at 1000 Hz, $\epsilon$=m/256). An implementation on a 41 MHz ARM7 microcontroller without a floating-point unit (Aduc7020, Analog Devices, Inc., Norwood Mass.) can generate estimates in real-time at 30 Hz (producing one estimate for every 33 input samples at 1000 Hz, $\epsilon$=m/64).

The derivation given here makes several simplifying assumptions about the form of the driving signal. The signal is assumed to be time-varying, but its relation to the surface EMG signal is not. Therefore there is no account for effects of fatigue, muscle length, velocity of shortening, temperature, or changes in skin conductance on the relation between driving signal and surface EMG signal. The statistical model of the driving signal is a Markov process, and therefore unable to model signals whose statistical properties change over time or depend upon random events in the remote past. There is no attempt to include sophisticated models of the relationship between force and the EMG signal (Lawrence and De Luca (1983) *J. Appl. Physiol.* 54: 1653-1659; Zhou and Rymer (2004) *J. Neurophysiol.* 92: 2878-2886), but such models could certainly be included when estimation of force is the goal.

For testing purposes, isometric contractions were used to match a known force that is less than 25% of maximum in order to: (1) provide a known "correct" answer that is related to both the muscle force and the voluntary activation of the muscle, (2) reduce potential effects of fatigue, and (3) eliminate effects of passive muscle and limb properties on the relation between torque and the EMG signal. For example, in a non-isometric task the relation between the EMG signal and the joint torque will be determined by many factors including limb inertia, the muscle length-tension and velocity-tension curves, and the geometry of the muscle-tendon attachments to bone. Since many of these relations are incompletely known for humans, non-isometric conditions cannot at this time be used to validate the filtering algorithm. However, one might hope that in the future the use of this algorithm to find an "equivalent isometric driving signal" during non-isometric tasks could be helpful to determine the relationship between the EMG signal and joint angle, angular velocity, and torque.

The above models may be modified in any way to reflect an intended use of the invention that is otherwise not explicitly claimed. Such modifications can be, for example, use with subjects having greater skin thickness, subjects having underlying adipose mass, levels of hirsuteness in the subject. In addition modification may be necessary for positioning the system of the invention in locations other than on the skin, for example, within the peritoneal cavity, the thoracic cavity, and the like. Modifications can also be made if the system is to be used to detect signals other than sEMG signals, such as detecting signals from small electronic devices and nanosystem devices where levels of signals perturbed due to signal-noise ratio may be difficult to monitor.

Successful use of surface electromyography for research, control, and biofeedback depends upon the quality, immediacy, and stability of the estimated signals. Given its assumptions, the Bayesian algorithm presented here will maximize the quality, immediacy, and stability over all other algorithms with similar assumptions. The algorithm produces adequate estimates from only a single electrode. Further work is needed to confirm its utility for control and biofeedback applications, and to include compensation for fatigue and other slow changes in the surface EMG signal (Park and Meek (1993) *IEEE Trans. Biomed. Eng.* 40: 1019-1023). Further work is also needed to investigate possible extensions to multi-electrode systems or to the estimation of other bioelectric signals. The ultimate goal is to provide an easily-implementable on-line estimation algorithm for bioelectric signals that can be used for research, medical treatment, and rehabilitation.

Hardware

The system described herein can be manufactured using a number of different components depending upon the intended use. Exemplary components are presented on FIG. 3. For uses where size is not a limitation, the system can be assembled using "off-the-shelf" components at a low cost. Such hardware can include, but is not limited to, sensors; amplifiers; transmitters; microprocessors; data storage devices and media, such as, but not limited to, discs, mass storage devices, molecular arrays, and the like; motors; acoustic amplifiers; acoustic speakers and generators; haptic devices; batteries; photoelectric cells; piezoelectric devices; such hardware for example, is readily available at the time of writing. For more diminutive systems, such as for use upon a limb or similar, smaller components will be used, and at times, the components can have multiple functions, such as for example, inclusion of a microprocessor with an electrode pair in a single device. Where extreme miniaturization is desirable, it is likely that the components will be manufactured using photolithographic technology or the like, thereby providing the components at a reduced cost. The power source can be a conventional battery, such as a lithium battery, or the power can be derived from an external source, such as using photon energy trapped using photoelectric cells, or the like. The components of the device and system can communicate with each other in a number of ways, for example, electric current along a metal wire or strip, wireless communication systems and devices, infra-red communications, ultrasonic communications, or the like. An exemplary circuit diagram for the electronic and electrical components of the invention are illustrated on FIG. 4. Any equivalents thereof can be used with the invention. In some cases, such as if a component that combines the function of two or more exemplary components as illustrated, some of the components as illustrated on FIG. 4 need not be included in the invention.

As disclosed herein, the system can comprise a wireless communication system that is used to transfer data from the sensor means and/or device to the processor and from the processor to the sensory output means and/or device. Further details on initialization and over the air programming techniques for a wireless sensors are described in greater detail in the patent applications of Mohammed Khair et al., Ser. No. 09/551,718 and Ser. No. 09/551,719, both filed on filed Apr. 18, 2000, which are incorporated by reference herein in their entirety.

The device or system can be placed upon the surface of the skin of a subject and can held in place using a number of different means, such as, but not limited to, straps, for example, self-adhesive straps, VELCRO (hook-and-eye) straps, buckles and straps; heat-activated adhesives; UV-activated adhesives; adhesive strips, magnetic strips, and the like.

The device or system can also comprise various motorized devices that stimulate or otherwise transfer motive forces, motive energy, or the like, to the surface of the subject's skin or muscle. These can be for example, but not limited to, a vibrator, a massager, a roller, a prosthetic limb device, a device for stimulating muscle such as a device for electrical stimulation or other artificial activation of muscle, a motorized bicycle, a motor scooter, a motor vehicle, a motorized aircraft, a motorized boat, and a motorized wheelchair.

Sensory Output

Audio Devices

Audio devices can be used with the invention to provided an aural or audio feedback to the patient or individual. The audio feedback allows the patient or individual to be aware of the amount and degree of muscle movement. Audio devices are well known to those in the art and can include speakers, resonators, and the like. Audio devices are particularly useful for patients or individuals having poor or impaired sight.

Visual Devices

Visual devices can be used with the invention to provided a visual feedback to the patient or individual. The visual feedback allows the patient or individual to be aware of the amount and degree of muscle movement. Visual devices are well known to those in the art and can include visual display units (VDUs), vacuum-tube televisions, flat-screen LCDs, flat-screen plasma systems, and the like. Visual devices are particularly useful for patients or individuals having poor or impaired hearing.

Haptic Devices

Haptics is the science of applying tactile or force sensation to human interaction with computers. A haptic device is one that involves physical contact between the computer and the user, usually through an input/output device, such as a joystick or data gloves, that senses the body's movements. By using haptic devices, the user can not only feed information to the computer but can receive information from the computer in the form of a felt sensation on some part of the body. This is referred to as a haptic interface. For example, in a virtual reality environment, a user can pick up a virtual tennis ball using a data glove. The computer senses the movement and moves the virtual ball on the display. However, because of the nature of a haptic interface, the user will feel the tennis ball in his hand through tactile sensations that the computer sends through the data glove, mimicking the feel of the tennis ball in the user's hand. Typical uses for a haptic interface are disclosed in U.S. Pat. No. 6,636,161 (Rosenberg, issued Oct. 21, 2003) and U.S. Pat. No. 6,697,043 (Shahoian, issued Feb. 24, 2004).

Applications and Significance

An important innovation is the explicit propagation of the conditional density through time. Rather than propagating only the estimate x(t) or a few elements of state, we propagate the entire conditional density p(x,t). We have developed an efficient algorithm for doing this in the discrete-time case, and the algorithm can be implemented on minimal hardware. The advantage of propagation of the probability density is that the ML estimate is available at any point in time.

In addition, the density can represent the degree of certainty in the estimate, and it can even represent a potential for more than one value of x(t) (for example, if the density is bilobed). Multiple possible values may occur near transitions and representation of this behavior allows for sudden and immediate changes in the output, rather than a restriction to slow, filtered outputs. Propagation of the density has been performed for diffusion processes, in fluid flow simulations, and possibly in other areas. In some cases, this is referred to as the Fokker-Planck equation. Our innovation is to use this propagation on a novel stochastic differential equation model and to develop a consistent, reliable, and rapid algorithm.

The algorithm may have broad applicability beyond its use for sEMG. Since sEMG approximates the product of a signal with white noise, our method will be applicable for any similar situation. For example, measurement of the output of noisy sensors, or measurement of population behavior or financial instruments may lead to models that are described by a product of the signal of interest (for example, temperature, consumer confidence) and noise (for example, random sensor variations, daily variation in goods purchased). Our method allows extraction of the signal of interest. Furthermore, it allows properties of the signal of interest to be specified in advance by appropriate design of the parameters of the generative model.

There are potential applications in radio electronics. Now that it is possible to demodulate a signal multiplied by noise, it is possible to create spread-spectrum transmissions that use low energy signals distributed over a wide region of available spectrum. ML estimation can be performed in either time-domain or frequency-domain in order to extract optimal estimates. When additive noise occurs, it merely adds a constant to the resulting estimate and will not affect audio-frequency and other common applications.

1. Research

The use of an explicit model based upon known features of physiology allows for extraction of a signal that may be a better representation of the intent of movement. Although movement may be variable, in fact the force generated by muscles is relatively constant and can be controlled smoothly. Our technique permits smooth yet rapid control and may therefore provide a better estimate than current linear methods.

2. Biofeedback

Rehabilitation: Biofeedback for rehabilitation has been used for many years with only limited success. One barrier was the social stigma of the feedback mechanism itself (often beeping). The use of vibration biofeedback solves this problem and may permit continual or prolonged use of the devices with consequent improved function. The success of biofeedback may depend critically upon the perception that the intent to move the muscle is immediately reflected in the feedback. The use of the ML estimation algorithm may be very helpful in this respect. In addition, it can be tuned to emphasize rapid changes, slow control, or to emphasize certain ranges of muscle activity over others.

Common use: Biofeedback is not commonly used, again due to social stigma. However, it has potential applications for the relief of muscle spasms, muscle tension, and tension-type headaches. The use of vibration biofeedback and the ML estimation algorithm may permit such applications 3. Control Rehabilitation engineering: An important innovation is that the generative model of sEMG can be designed so that the resulting control signal is appropriate for control of the particular task. For instance, if sEMG is used for steering then smooth control will be more important than fast jumps. On the other hand, if sEMG is used for musical performance, then fast jumps must be possible whenever needed. It is generally assumed that the quality of sEMG signals is inadequate for generating smooth proportional control. Our algorithm allows smooth control, and therefore solves this problem. This is the first algorithm to be able to provide reliable proportional control from a single electrode. It could therefore be an important component in future assistive technology (for mobility or communication) and it could be essential in permitting the design of controllable prostheses.

Conditions and disorders resulting in loss of muscular activity and/or control include, but are not limited to, neurological disorders, such spinal cord injury, amyotrophic lateral sclerosis, and stroke, limb loss, muscle loss, muscle fatigue, loss of motor neuron activity, and loss of neural tissue.

Other control applications: In situations in which humans must control many systems with only minimal movement (aircraft control, for instance) it may be helpful to be able to use sEMG as an adjunctive actuator technology. Since the sEMG signal increases prior to the onset of movement, recording sEMG may be used to reduce the effective reaction time. For example, a driver who activates the brake suddenly will require at least 50 ms to achieve full muscle force following sEMG activation. If sEMG were identified earlier, the reaction time might be decreased.

4. Electronic Communications

The non-linear filtering algorithm can also be used for demodulating broad spectrum radio waves, for example, used for encryption and used for "cleaning-up" noisy channels to improve a received signal.

There are many possible variations on this idea, including other forms of local tactile input (small electrical currents, touch, temperature, pressure, etc.) The innovation is that there should always be feedback near the site bf the sEMG electrode itself. The technique can be implemented using either linear estimation methods or ML estimation methods.

This idea may have widespread application beyond the field of rehabilitation. For example, unimpaired adults with chronic neck pain, back spasms, or tendonitis may benefit from an unobtrusive device that provides a continual reminder of the need to relax, while at the same time vibrating (and thereby massaging) muscles in spasm. Athletes who seek to modify a pattern of movement, either to relax inefficient muscles or enhance contraction of agonist muscles could benefit from training with such a device.

Other uses for the system and methods disclosed herein are, for example, use in pedometers and the like, for example, devices that measure and record activities that have very low threshold signal output, such as an infant monitor.

The invention will be more readily understood by reference to the following examples, which are included merely for purposes of illustration of certain aspects and embodiments of the present invention and not as limitations.

EXAMPLES

Example I

Software Implementation

```
poisson_spread = 1.0;
    for (i= 0 ; i<NOUTPUTS ; i++) {
        fprior[i] = 1.0 / NOUTPUTS;
        expx[i] = exp(- ((double) i) / (NOUTPUTS *       //for
        poisson_spread));
poisson calculation
    }
        fzero = 0.0;
    expx[0] = 1.0;
        while (1) {
            favgval = fvarest = 0.0;
            /* read the ADC and average over blocklength */
            for (i=0 ; i<BLOCKLENGTH ; i++) {
                fval = read_ADC(1);
                fzero = 0.99 * fzero + 0.01 * fval;
                fvarest += fabs(fval - fzero);
                //fval -= fzero;
                //favgval += fval;
            }
            fvarest *= 1.0E1;
```

```
        fvarest /= BLOCKLENGTH;
        mlest = 0;
        fmaxprior = fsumprior = 0.0;
        /* read current settings from parameter potentiometers */
        drift = 1.0 * read_ADC(3);     //.06    //adc3 on pin 1
        shift = .001 * read_ADC(4); //.00007 (.0003 for 16level)
        input_gain = 2.7 * 10.0 * read_ADC(0); // pot on
        arm7//10.0 *
read_ADC(3); //2.7
        fvarest *= input_gain; //adc4 on pin 2
        //propagate the probability density
        for (i= 0 ; i<NOUTPUTS ; i++)
        {
            lambda = ((double) i) / (NOUTPUTS *
            poisson_spread);
            x = fvarest / poisson_spread;
            fprior[i] *= pow(lambda, x) * expx[i]; //poisson
        }
        temp = fprior[0];
        for (i=0 ; i<NOUTPUTS ; i++)
        {
                if (i>1)
                { //Drift gradually
                    temp = fprior[i−1];
                    fprior[i−1] += drift * (temp + fprior[i]);
                    //blurring
                }
                fprior[i] = shift + (1.0−shift) * fprior[i];
//probability of sudden shifts
                fsumprior += fprior[i];
                if (fprior[i] > fmaxprior)
                { //ML estimate
                    mlest = i;
                    fmaxprior = fprior[i];
                }
        }
        //renormalize the density
        fprior[NOUTPUTS−1] /= 4.0; //gets stuck here...
        for (i=0 ; i<NOUTPUTS ; i++) fprior[i] /= fsumprior;
        if (mlest > 0 && mlest < NOUTPUTS−1)
        {
            fmlest = fprior[mlest−1] * (mlest−1.0) + fprior[mlest] *
            ((float)
mlest) + fprior[mlest+1] * (mlest+1.0);
            fmlest /= (float) fprior[mlest−1] + fprior[mlest] +
fprior[mlest+1];
            {
            else fmlest = (float) mlest;
```

Note that this algorithm can be implemented very rapidly in hardware without the use of a microprocessor. The current estimate of probability can be stored on a bank of capacitors, and each capacitor can be charged by a specific level of input determined by the use of one or more comparators.

Example II

Hardware Implementation

Figure 3:
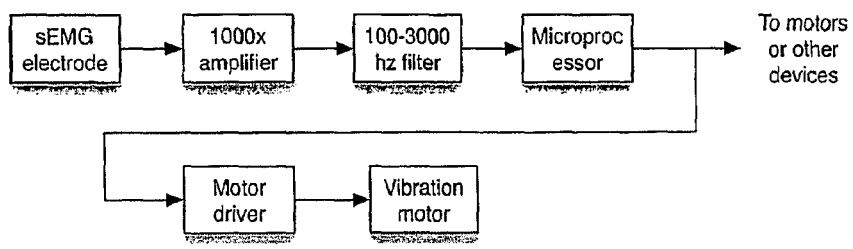
FIG. 3 shows exemplary hardware systems used with the invention.
Figure 4:
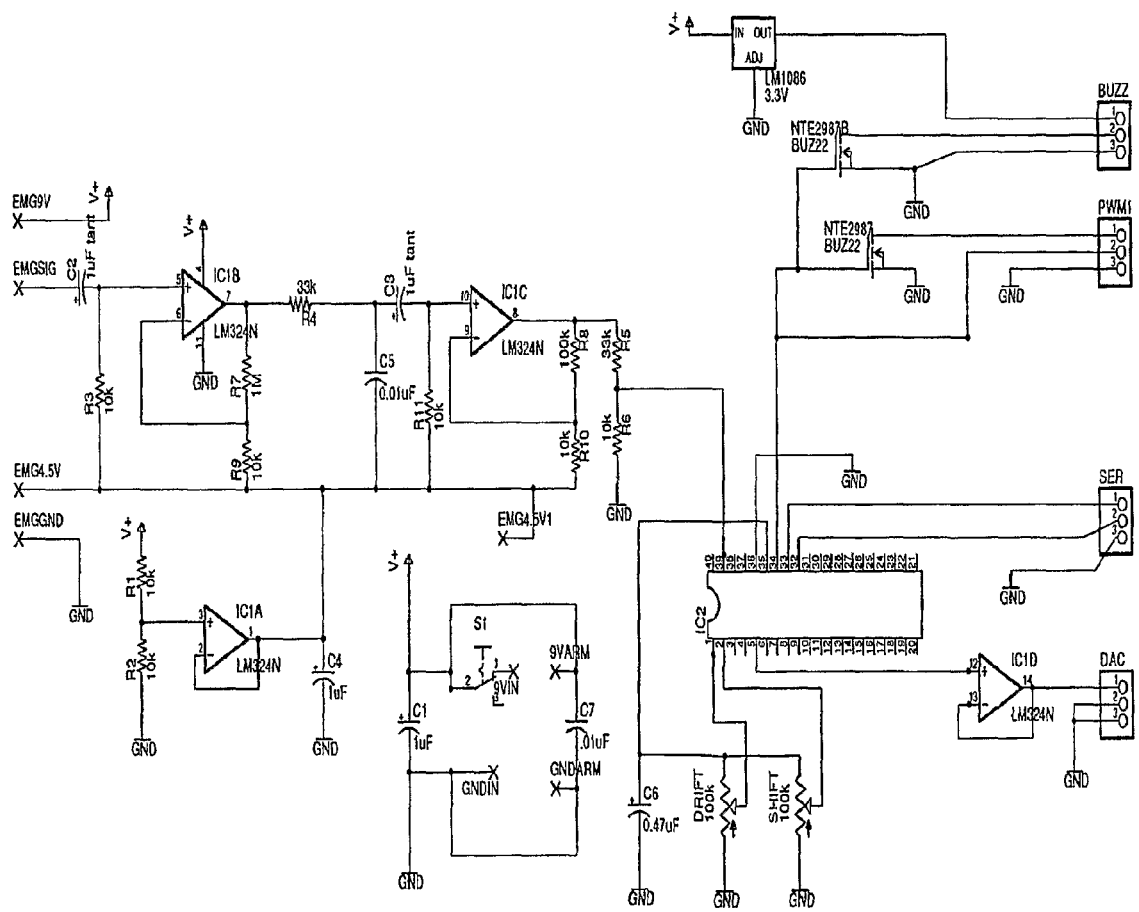
FIG. 4 shows an exemplary circuit diagram used with the invention.

Most sEMG is recorded with bandpass filters set between 20 Hz and 500 Hz. However, the ML estimation algorithm performs well with higher frequencies, and the low frequencies are less likely to be helpful since they do not contain information on rapid change, and long observation intervals are required to estimate the power in low frequency data. Therefore bandpass filters from 100 Hz to 1500 Hz, with sample rates of 3000 Hz or higher were used. FIG. 3 illustrates a summary of the hardware used with the invention. Two electrodes for detecting EMG signals were used. The electrodes were encased in a first box. The electrodes were in electrical communication using wire with the amplifier, the filter, and the microprocessor; the amplifier, the filter, and the microprocessor were encased in a second box. The microprocessor was in electrical communication using wire to the motor driver and the vibration motor. The motor vibration motor was adhered to the first box that encased the electrodes. FIG. 4 illustrates a summary of the electrical circuit used with the invention.

Example III

MAP Estimation

If a series of measurements of sEMG(t) and a corresponding series of measurements of some other value (such as force) are available, then it is possible to use maximum a posteriori (MAP) estimation to derive estimates without the need for a stochastic model. In this case, any density estimation algorithm (such as kernel density estimators) can be used to estimate the conditional densities p(force(t)|sEMG(t−d)) for arbitrary values of d. When d is sufficiently large, force and sEMG will be unrelated, so there is a finite time horizon D for which the conditional density will be non-constant. Assume that the measurements of sEMG are conditionally independent given the force, so that $$p(sEMG(t1),sEMG(t2)|\text{force}(t))=p(sEMG(t1)|\text{force}(t)) \\ p(sEMG(t2)|\text{force}(t)) \quad (36)$$

When this is the case we can write:

$$p(\text{force}(t))=p(\text{force}|sEMG(t))p(\text{force}|sEMG(t-1))\ldots \\ p(\text{force}|sEMG(t-D)) \quad (37)$$

This gives a model-free MAP estimate of force. The process depends upon having a sufficient number of examples such that the conditional densities can be estimated in advance. It also depends upon the assumption of conditional independence. The assumption will be approximately valid whenever the sampling rate is low compared with the lowest frequency present in the sEMG signal, and this can be made more likely by bandpass filtering the sEMG. Alternatively, corrections to the product above can be made in order to take into account some degree of lack of independence.

Example IV

Vibration Feedback

When sEMG is used for biofeedback, the user must be provided with a sensory feedback that can be used to determine whether the task is being performed correctly or not. Frequently, this feedback is in the form of an auditory signal such as beeping or a visual signal such as a blinking light. However, such feedback is often difficult to use, and there are large delays in auditory or visual processing. Perhaps most importantly, it is distracting to the user, requiring constant attention, and it is distracting to others around the user. Therefore biofeedback is only used in a therapy setting and is almost never possible on a more constant basis within the school or workplace. Nevertheless, more constant use will have significantly greater benefits.

When sEMG is used for control, subjects must identify the particular muscle that is being used to drive the external electromechanical device. For subjects with reduced cognitive abilities, this may be extremely difficult. For example, a child who is unaware of what a "biceps" is, or who does not have the ability to independently control activity in the biceps, may be at a complete loss when provided with a machine controlled by biceps activity.

Therefore both biofeedback and control applications would benefit from a form of feedback that is immediate, quiet, and salient without being distracting, and closely related to the muscle that provides the control. It is proposed to use vibration of the same muscle that is used for measurement of sEMG as the feedback signal. This is accomplished by the use of a small vibrating motor attached directly to the sEMG electrode. The motor is driven by the ML estimation algorithm above, and speed is controlled using pulse-width modulation with the pulse width controlled by the estimated value of x(t). Vibration may be used in addition to any other form of feedback. For example, the muscle may be vibrated, and a light, sound, game, or other task may be activated simultaneously. The vibration indicates the muscle that is providing the control, and the task provides the parameters of control that the subject must achieve.

Example V

Subjects and Data Collection

Five healthy right-handed adult subjects between 22 and 26 years of age (four male, one female) were recruited and all signed written informed consent to participate as well as US Health Information Portability and Accountability Act (HIPAA) authorization for use of medical and research records, according to approval of the Stanford University Institutional Review Board.

Subjects were seated comfortably and positioned with straps in an adjustable chair (Biodex Medical Systems, Shirley N.Y.), and their right arm was strapped into a custom-built aluminum frame. The arm was positioned with the elbow at ninety degrees and placed at shoulder height, forty-five degrees from the sagittal plane. The forearm was vertical, and attached using VELCRO straps to a load cell (Interface Inc., Scottsdale Ariz., model 1500ASK-50). Surface EMG electrodes (Delsys Inc., Boston Mass., model DE2.3) were attached over the belly of the biceps and triceps muscle. These electrodes have a gain of 1000 and bandpass frequency response from 20-450 Hz. Force and EMG data were digitized simultaneously at 1000 Hz (Cambridge Electronic Design Ltd, Cambridge UK, model Power 1401), and data were stored offline for subsequent analysis.

The force during maximum voluntary elbow flexion (MVC) was measured for each subject as the maximum value over three attempts of at least 5 seconds each. Subsequently, each subject performed thirty trials of 6 seconds each. On each trial, subjects initially were required to maintain relaxation (confirmed by EMG signal and force measurement). They were then asked to attempt to flex the elbow (against the isometric constraint) in order to match a desired force level. Most subjects required less than 1 second to achieve a steady-state force. The target level was displayed on a monitor by a horizontal line, and the actually achieved force level was also displayed, so that subjects could match the two lines. Target forces of 2.5, 5, 10, 15, 20, and 25 percent of MVC were used in pseudo-random order with 5 trials at each force level. Low forces were chosen to avoid fatigue, and 1-2 minutes of rest were given between trials. Subjects were asked to state if they felt fatigued, but this did not occur.

Example VI

Statistical Analysis

Computations were performed using MATLAB (Mathworks, Natick Mass.), and statistical analyses were performed using R (R project group). Performance was compared with two standard linear algorithms. The first algorithm was a lowpass filter applied to the rectified EMG signal, with cutoff frequencies of 5 Hz, 1 Hz, or 0.1 Hz. Low-pass filters of order 1000 were calculated using the firl function in MATLAB, and filtering was applied separately to the biceps and triceps EMG signal. The second algorithm was the optimal linear estimator of torque given the rectified EMG signal from both biceps and triceps. For each subject and each trial, the optimal $100^{th}$-order finite-impulse-response (FIR) linear filter was calculated using the Steiglitz-McBride method (stmcb function in MATLAB).

Bayesian decoders were implemented with the Poisson, Half-Gaussian, and Exponential measurement models. Each of the Bayesian decoders produced a separate estimate for biceps and triceps activation levels. In order to estimate torque, the best linear estimate of torque from the two activation levels was calculated using linear regression for each task condition for each subject, and for each of the two algorithms. Linear regression was performed time point by time point, so that there were only two scalar regression coefficients (for biceps and triceps) for each subject and each task condition.

The ability to estimate torque was used as the primary outcome measure since the subjects had been instructed to produce a specified torque level. Therefore torque was considered to be a surrogate measure of the intended muscle activation level.

The root mean square error (RMSE) for estimated torque was calculated for each of the algorithms, for each task and each subject. Signal to noise ratio (SNR) was calculated as the average squared torque divided by the mean squared error. The correlation coefficient $r^2$ between measured torque and the estimated torque was also calculated. Values of SNR, RMSE, and $r^2$ were compared between algorithms using a pairwise two-tailed Student's t-test. Results for the primary outcome (SNR) were reported as significant for $p<=0.05$.

Example VII

Results

The relation between the mean and variance of the raw EMG signal can be used to assess the relative goodness of fit of the different EMG signal models.

Figure 5:
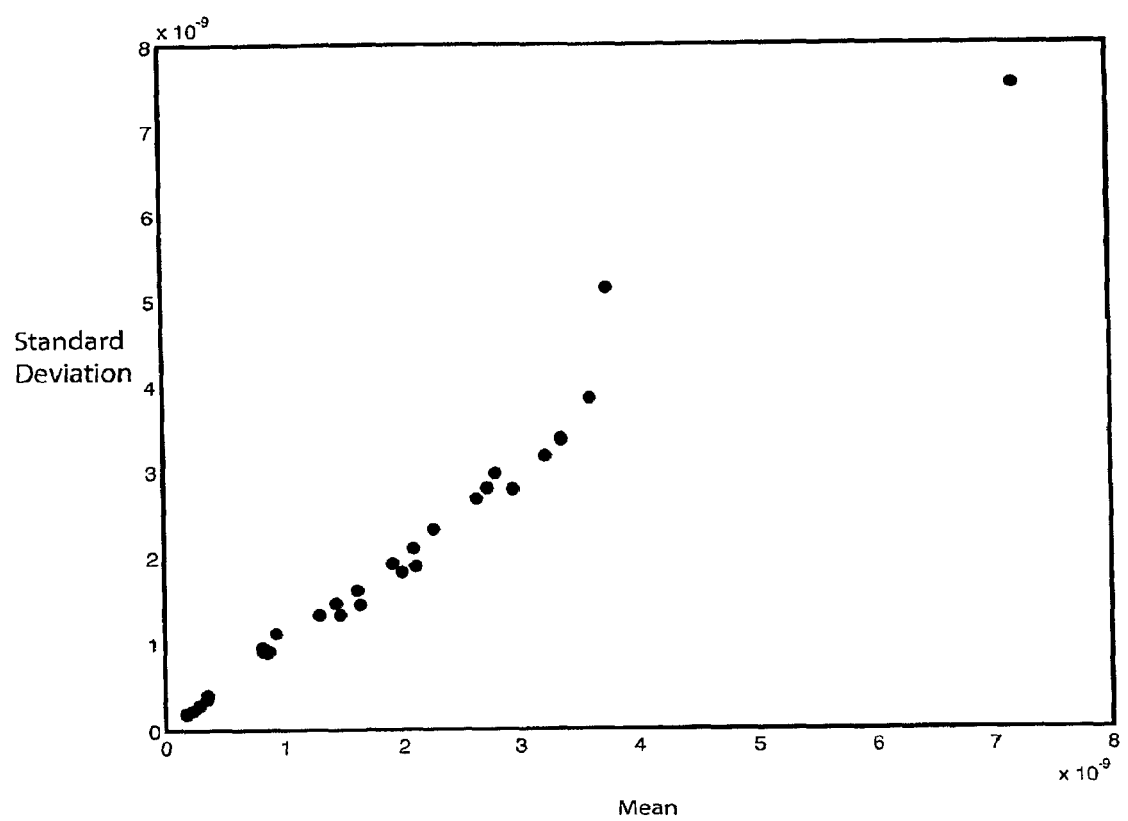
FIG. 5 illustrates a plot of the standard deviation of biceps EMG signal versus the mean for all subjects and all MVC levels. Each point represents a single trial for one subject.

FIG. 5 shows a plot of the standard deviation vs. the mean of the raw biceps EMG signal over all subjects and all MVC levels. The correlation coefficient ($r^2$) is 0.97. The quality of the linear fit can be assessed by regression of log(variance) on log(mean), which produces a slope of 1.98 (confidence interval 1.91-2.06) consistent with a linear relationship between the mean activity and the square root of the variance (the standard deviation). Note that the standard deviation is proportional to the mean for an exponential distribution or a half-Gaussian distribution, but not a Poisson distribution (for Poisson, the variance is proportional to the mean). This suggests that the Poisson model is a poor fit to these data, but that either the exponential of half-Gaussian models could be appropriate estimators.

Figure 6:
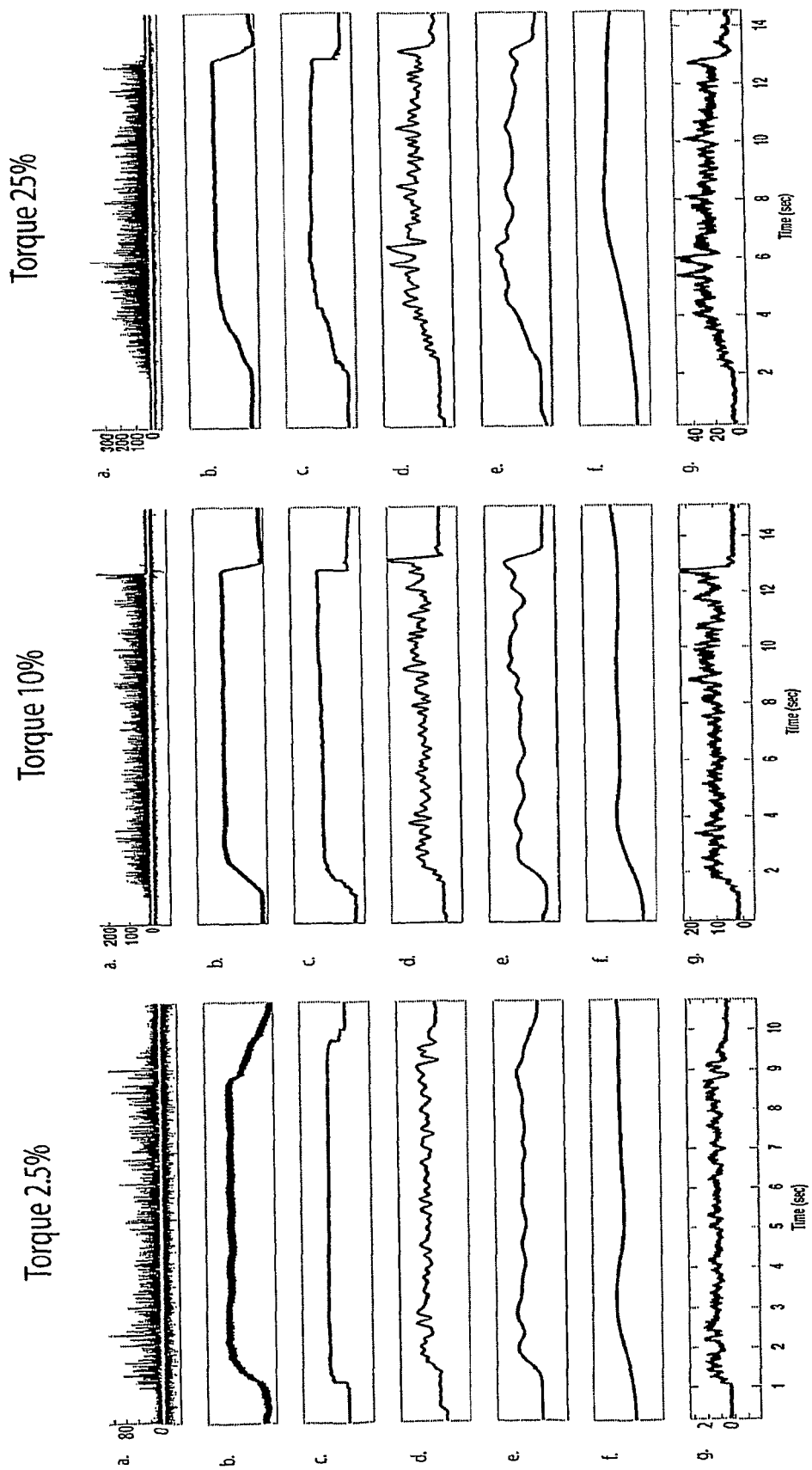
FIG. 6 shows examples of estimates from different algorithms for a single subject. Left: single trial at 2.5% of maximal voluntary torque; Middle: 10% of maximal torque; Right: 25% of maximal torque. a: Raw EMG signal (in mV) of biceps (upward from midline) and triceps (downward from midline). b: Torque, in percent maximum voluntary elbow flexion (MVC) with flexion upward. c: Bayes nonlinear estimator using exponential distribution assumption. d, e, f: Linear low-pass filter applied to the rectified EMG signal with cutoff at 5 hz, 1 hz, and 0.1 hz respectively. g: Optimal finite impulse response linear filter of order 100. Traces b through g use the same scale for each torque level.

FIG. 6 shows sample plots of the raw EMG signal, the measured torque, and the estimates from several different algorithms. The mean values of signal to noise ratio (SNR), root mean squared error (RMSE), and correlation coefficient ($r^2$) are shown in Table 1. The Bayesian algorithm assuming an exponential or half-Gaussian distribution on the input performed significantly better (Student's t-test) in all three measures compared with all other algorithms. The Bayesian algorithm with exponential distribution was significantly different from the half-Gaussian distribution only for SNR.

Figure 7:
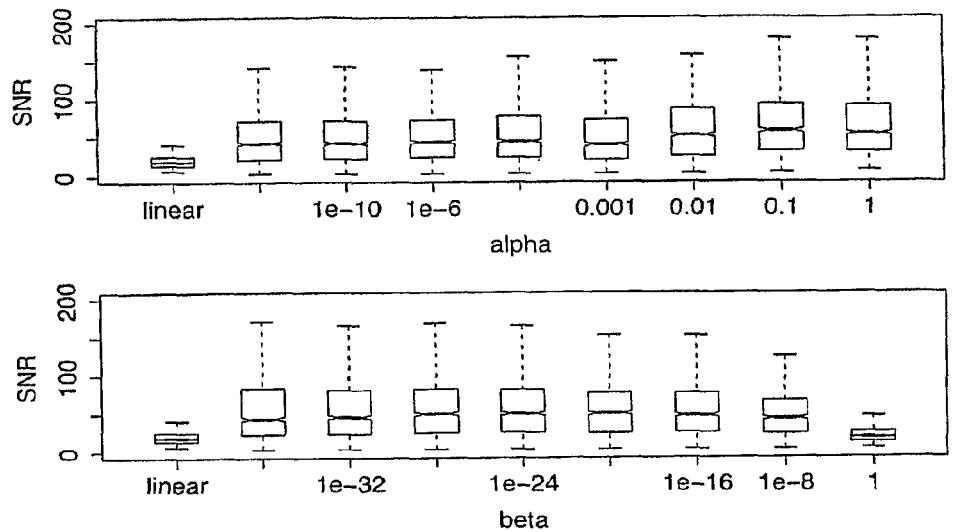
FIG. 7 illustrates the sensitivity of the nonlinear Bayesian algorithm with exponential electromyography model to changes in parameters. Top: different values of alpha (beta=$10^{-24}$). Bottom: different values of beta (alpha=0.001). Gray box indicates +/−1 SD, whiskers indicate extreme values of data.

FIG. 7 shows the relative performance of the Bayesian algorithm with exponential input distribution for varying values of the parameters $\alpha$ and $\beta$. The SNR does not change significantly over many orders of magnitude, and SNR is significantly different from the best linear algorithm ($p<0.0001$ compared to 1 Hz filter by paired t-test) for all cases except $\beta=1$ ($p=0.074$).

Figure 8:
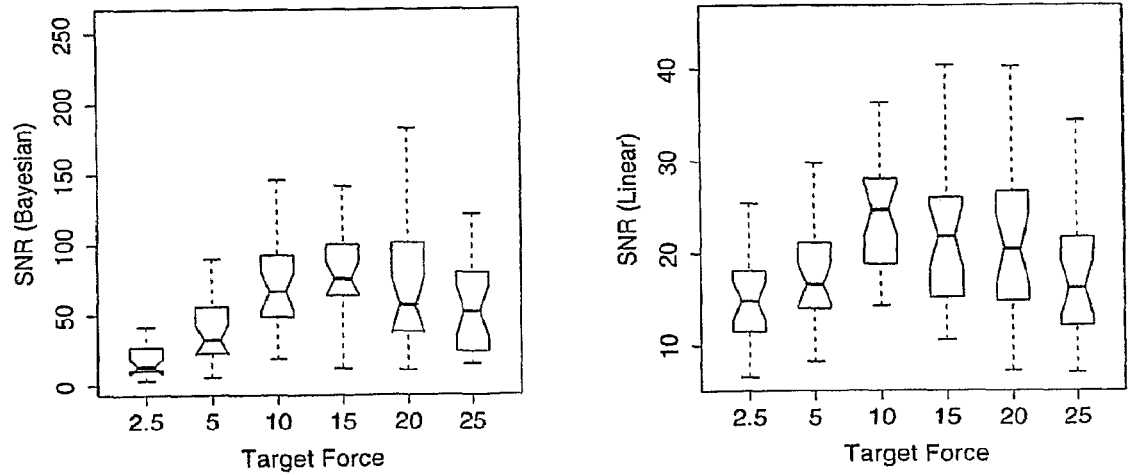
FIG. 8 illustrates the performance of the Bayesian (exponential model, alpha=0.001, beta=$10^{-24}$) and linear (1 Hz low-pass filter) algorithms model for different values of the target force. Force is given in percent of the maximum voluntary contraction for each subject.

FIG. 8 shows the relative performance of the Bayesian and linear (1 Hz) algorithms with $\alpha=0.001$, $\beta=10^{-24}$ for each of the different levels of target force. The SNR for the Bayesian algorithm is significantly higher (p<0.001) for all values of force except 2.5% (p=0.11).

Example VIII

Analysis of Data

The relation between the standard deviation and the mean of the EMG signal (FIG. 5) is most consistent with either an exponential or a half-Gaussian model for the measurement. This may explain the relatively better performance of the Bayesian algorithm when using either of these measurement models compared with the Poisson measurement model. In all cases, the Bayesian algorithm outperforms the linear algorithms, as shown in Table 1. For example, the Bayesian algorithm with the exponential measurement model improves the signal-to-noise ratio of the estimate by a factor of three compared with the best linear model. Note that the "optimal" linear estimator did not perform as well as the 1 Hz low-pass filter, and this is most likely due to the 100-point time-window used by the optimal estimator (vs. the 1000-point time-window of the low-pass filter). An estimator with a longer time-window may perform better, but estimation of the parameters of a 1000th-order optimal finite impulse response filter would require a much larger amount of data per trial than was available.

TABLE 1

Comparison of performance between different algorithms

| Method | Signal-to-Noise Ratio | Root Mean Square Error | $r^2$ |
|---|---|---|---|
| Low-pass, 5 Hz | 10.95 +/− 0.28 *** | 0.236 +/− 0.0027 *** | 0.624 +/− 0.0097 *** |
| Low-pass, 1 Hz | 19.80 +/− 0.64 *** | 0.180 +/− 0.0029 *** | 0.777 +/− 0.0079 *** |
| Low-pass, 0.1 Hz | 8.77 +/− 0.44 *** | 0.276 +/− 0.0042 *** | 0.497 +/− 0.0119 *** |
| Optimal | 13.41 +/− 0.49 *** | 0.219 +/− 0.0034 *** | 0.688 +/− 0.0116 *** |
| LinearBates/Poisson | 38.71 +/− 3.02 *** | 0.154 +/− 0.0048 *** | 0.816 +/− 0.0124 ** |
| Bayes/Half-Gaussian | 46.98 +/− 2.46 * | 0.135 +/− 0.0046 NS | 0.856 +/− 0.0118 NS |
| Bayes/Exponential | 58.46 +/− 3.71 | 0.125 +/− 0.0046 | 0.872 +/− 0.0117 |

Values are means +/− SE. Significance of differences from the Bayes/Exponential algorithm are indicated as
* p < 0.01,
** p < 0.001,
*** p < 0.0001,
NS: not significant.

Comparison of the Bayesian algorithm with linear methods in FIG. 6 shows that the Bayesian algorithm has more rapid response to EMG signal onset and offset. In most cases, changes at the output of the Bayesian filter precede changes in torque, since the Bayesian filter has the ability to produce changes in output that are more rapid than the mechanical response. Thus the rate of rise of the torque estimate can be more rapid than the rate of rise of the measured torque.

FIG. 7 shows that the signal to noise ratio of the Bayesian algorithm is relatively insensitive to the particular values of its parameters. However, changes in the parameters will affect the smoothness of the filtered result, so these parameters should be chosen to match the intended purpose of the output. In particular, for estimation of torque they should be chosen to match the statistics of torques that actually occur. For control of a motor they should be chosen to match the capabilities of the motor.

FIG. 8 shows that both the Bayesian and linear (1 Hz) algorithms perform best at target force between 10% and 20% of maximum voluntary force. One reason for this may be that the exponential model for the EMG signal provides a better fit in this range. Another reason may be that the higher energy in the signal provides more information per unit time for estimation.

Those skilled in the art will appreciate that various adaptations and modifications of the just-described embodiments can be configured without departing from the scope and spirit of the invention. Other suitable techniques and methods known in the art can be applied in numerous specific modalities by one skilled in the art and in light of the description of the present invention described herein. Therefore, it is to be understood that the invention can be practiced other than as specifically described herein. The above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

I claim:

1. A biofeedback device adapted for using the activity of one or more muscles to proportionally control a second electromechanical device, the biofeedback device comprising a first detector configured for detecting a first signal that indicates a time series of surface electromyography measurements, designated sEMG(t), for each time t of a plurality of times from a particular location on a subject, a processor configured for processing the first signal using a nonlinear filter for determining a time series of a stable driving signal x(t), a power source, and a feedback system, the feedback system comprising a motorized device, wherein the feedback system is in electrical communication with the processor, wherein processing the first signal using the nonlinear filter further comprises applying a nonlinear filter that includes a first parameter α that indicates a rate of drift for values of x(t) and an independent second parameter β that indicates frequency of shift in values of x(t); and the feedback system causes the motorized device to apply a sensory feedback to the subject based on the stable driving function.

2. A biofeedback device as recited in claim 1, wherein the feedback system applies sensory feedback in a vicinity of the particular location.

3. A biofeedback device as recited in claim 2, wherein the feedback system applies a vibration as the sensory feedback.

4. A biofeedback device as recited in claim 3, wherein the first detector is an sEMG electrode and the motorized device comprises a substantively quiet, small vibrating motor adhered to a box that encases the sEMG electrode.

5. A biofeedback device as recited in claim 4, wherein:
the biofeedback device is portable; and
the feedback system applies the vibration on a constant basis compared to a therapy setting.

6. A biofeedback device as recited in claim 5, wherein the biofeedback device excludes audio beeping and a visual signal.

7. A biofeedback device as recited in claim 3, wherein the biofeedback device is configured for:
attaching to the subject that has a condition selected from a group comprising cerebral palsy, brain damage resulting from head trauma, brain damage resulting from oxygen deprivation, paraplegic loss of all or part of a limb, spinal cord injury, amyotrophic lateral sclerosis, stroke, AIDS, sarcopenia, disuse atrophy, glucocorticoid induced muscle loss, prolonged spaceflight, chronic neck pain, back pain, and muscle spasms, muscle tension, tension-type headache and athletic training; and
operating the motorized device to effectively treat the condition.

8. A biofeedback device as recited in claim 2, wherein determining the stable driving signal x(t) is performed in real time.

9. A biofeedback device as recited in claim 2, wherein to apply the sensory feedback to the subject based on the stable driving function further comprises driving a motorized prosthetic device attached to the subject in the vicinity of the particular location.

10. A biofeedback device as recited in claim 1, wherein to apply the sensory feedback to the subject based on the stable driving function further comprises operating a device based on the stable driving function, wherein the subject is able to sense the operation of the device.

11. A biofeedback device as recited in claim 1, wherein applying the nonlinear filter further comprises applying a recursive method comprising:
determining a measurement model, designated P(emg|x), that relates the probability of a rectified sEMG observation, designated emg, given a value of the stable driving signal x;
determining a probability density function of values for the stable driving signal x at each time ti, designated p(x,ti), based on previous measurements sEMG(ti) at previous times ti<t;
propagating the probability density p(x,t−Δt) forward in time an amount Δt to time t to provide an a priori probability density function for the stable driving signal x at time t, designated p(x,t−);
determining a posteriori probability density function of a value of x at time t, designated P(x,t), based on P(emg|x) and p(x, t−); and
determining an output value x(t) substantively equal to maximum a posteriori (MAP) value for x that has the highest a posteriori probability, designated argmax(P(x, t)).

12. A biofeedback device as recited in claim 11, wherein determining the probability density function of values for the stable driving signal x at initial time t0 before a first measurement of sEMG(t) further comprises determining a constant probability density for an expected range of values of x.

13. A biofeedback device as recited in claim 11, wherein propagating the probability density p(x,t−Δt) forward in time further comprises:
determining a value ε for bin width of a histogram that represents the probability density function of values for the stable driving signal x; and
evaluating an equation given by $$p(x,t-) = \alpha p(x-\epsilon, t-\Delta t) + (1-2\alpha) p(x, t-\Delta t) + \alpha p(x+\epsilon, t-\Delta t) + \beta + (1-\beta) p(x, t-\Delta t).$$

14. A biofeedback device as recited in claim 11, wherein determining the measurement model further comprises selecting the measurement model from a group comprising a Poisson measurement model and a half-Gaussian measurement model and an exponential model.

15. A biofeedback device as recited in claim 11, wherein applying the recursive method further comprises determining p(x,t) by dividing P(x,t) by a constant C, such that ∫ p(x,t) dx =1.

16. A method comprising:
obtaining a time series of surface electromyography measurements sEMG(t) for each time t of a plurality of times from a particular location on a subject;
determining on a processor a time series of a stable driving signal x(t) based on the measurements sEMG(t), further comprising applying a nonlinear filter that includes a first parameter α that indicates a rate of drift for values of x(t) and an independent second parameter β that indicates frequency of shift in values of x(t); and
applying a sensory feedback to the subject based on the stable driving function.

17. A method as recited in claim 16, wherein applying the sensory feedback to the subject based on the stable driving function further comprises applying the sensory feedback in a vicinity of the particular location.

18. A method as recited in claim 17, wherein applying the sensory feedback to the subject based on the stable driving function further comprises applying a vibration as the sensory feedback.

19. A method as recited in claim 18, wherein applying the vibration as the sensory feedback further comprises driving a substantively quiet, small vibrating motor adhered to a box that encases a sEMG electrode.

20. A method as recited in claim 19, wherein:
a portable system comprises the sEMG electrode, the vibrating motor, a processor configured for determining the stable driving signal x(t), and a battery for powering the vibrating motor and processor; and
applying the vibration as sensory feedback further comprises applying the vibration as sensory feedback by the portable system for a prolonged time compared to a therapy setting.

21. A method as recited in claim 20, wherein the portable system excludes audio beeping and a visual signal.

22. A method as recited in claim 18, wherein:
the method further comprises selecting the subject, wherein the subject is determined to have a condition selected from a group comprising cerebral palsy, brain damage resulting from head trauma, brain damage resulting from oxygen deprivation, paraplegic loss of all or part of a limb, spinal cord injury, amyotrophic lateral sclerosis, stroke, AIDS, sarcopenia, disuse atrophy, glucocorticoid induced muscle loss, prolonged spaceflight, chronic neck pain, back pain, and muscle spasms, muscle tension, tension-type headache and athletic training; and
applying the vibration further comprises applying the vibration to effectively treat the condition.

23. A method as recited in claim 17, wherein determining the stable driving signal x(t) is performed in real time.

24. A method as recited in claim 17, wherein applying the sensory feedback to the subject based on the stable driving function further comprises driving a motorized prosthetic device attached to the subject in the vicinity of the particular location.

25. A method as recited in claim 16, wherein applying the sensory feedback to the subject based on the stable driving function further comprises operating a device based on the stable driving function, wherein the subject is able to sense the operation of the device.

26. A method as recited in claim 16, wherein applying the nonlinear filter further comprises applying a recursive method comprising:
   determining a measurement model, designated P(emg|x), that relates the probability of a rectified sEMG observation, designated emg, given a value of the stable driving signal x;
   determining a probability density function of values for the stable driving signal x at each time ti, designated p(x,ti), based on previous measurements sEMG(ti) at previous times ti<t;
   propagating the probability density $p(x, t-\Delta t)$ forward in time an amount $\Delta t$ to time t to provide an a priori probability density function for the stable driving signal x at time t, designated p(x,t−);
   determining a posteriori probability density function of a value of x at time t, designated P(x,t), based on P(emg|x) and p(x, t−); and
   determining an output value x(t) substantively equal to maximum a posteriori (MAP) value for x that has the highest a posteriori probability, designated argmax(P(x, t)).

27. A method as recited in claim 26, wherein determining the probability density function of values for the stable driving signal x at initial time t0 before a first measurement of sEMG(t) further comprises determining a constant probability density for an expected range of values of x.

28. A method as recited in claim 26, wherein propagating the probability density $p(x, t-\Delta t)$ forward in time further comprises:
   determining a value $\epsilon$ for bin width of a histogram that represents the probability density function of values for the stable driving signal x; and
   evaluating an equation given by $$p(x,t-) = \alpha p(x-\epsilon, t-\Delta t) + (1-2\alpha) p(x, t-\Delta t) + \alpha p(x+\epsilon, t-\Delta t) + \beta + (1-\beta) p(x, t-\Delta t).$$

29. A method as recited in claim 26, wherein determining the measurement model further comprises selecting the measurement model from a group comprising a Poisson measurement model and a half-Gaussian measurement model and an exponential model.

30. A method as recited in claim 26, wherein applying the recursive method further comprises determining p(x,t) by dividing P(x,t) by a constant C, such that $\int p(x,t) dx = 1$.

* * * * *